US 7,534,597 B2

(12) United States Patent
Hause et al.

(10) Patent No.: US 7,534,597 B2
(45) Date of Patent: *May 19, 2009

(54) METHODS AND MATERIALS FOR THE PRODUCTION OF L-LACTIC ACID IN YEAST

(75) Inventors: Ben Hause, Jordan, MN (US); Vineet Rajgarhia, Minnetonka, MN (US); Pirkko Suominen, Maple Grove, MN (US)

(73) Assignee: Cargill, Inc., Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/452,038

(22) Filed: May 30, 2003

(65) Prior Publication Data
US 2003/0228671 A1   Dec. 11, 2003

Related U.S. Application Data

(60) Provisional application No. 60/384,333, filed on May 30, 2002.

(51) Int. Cl.
| | | |
|---|---|---|
| C12N 1/19 | (2006.01) | |
| C12N 1/00 | (2006.01) | |
| C12N 15/70 | (2006.01) | |
| C12Q 1/68 | (2006.01) | |
| C12N 15/63 | (2006.01) | |

(52) U.S. Cl. .................. 435/254.2; 435/6; 435/254; 435/1; 435/471

(58) Field of Classification Search .................. None
See application file for complete search history.

(56) References Cited

U.S. PATENT DOCUMENTS

| | | | |
|---|---|---|---|
| 5,332,668 A * | 7/1994 | Yamashita et al. | .......... 435/223 |
| 5,849,524 A | 12/1998 | Kondo et al. | |
| 6,046,002 A * | 4/2000 | Davis et al. | .................... 435/6 |
| 6,110,725 A | 8/2000 | Delley et al. | |
| 6,268,189 B1 | 7/2001 | Skory | |
| 6,429,006 B1 | 8/2002 | Porro | |
| 6,485,947 B1 | 11/2002 | Rajgarhia et al. | |
| 2003/0166179 A1 | 9/2003 | Rajgarhia et al. | |
| 2003/0190630 A1* | 10/2003 | Rajgarhia et al. | ............... 435/6 |

FOREIGN PATENT DOCUMENTS

| | | | |
|---|---|---|---|
| WO | WO 99/14335 | * | 3/1999 |
| WO | WO 00/71738 A1 | | 11/2000 |
| WO | WO 02/42471 A2 | | 5/2002 |
| WO | WO 02/42471 A3 | | 5/2002 |
| WO | WO 03/102201 A3 | | 12/2003 |

OTHER PUBLICATIONS

Holloway et al. The isolation and nucleotide sequence of the pyruvate decarboxylase gene from *Kluyveromyces marxianus*. Curr. Genet. 24: 274-277, 1993.*

Bhowmik et al. Cloning, characterization and insertional activation of the *Lactobacillus helveticus* D(-) lactate dehydrogenase gene. Appl. Microbiol. Biotechnol. 41: 432-439, 1994.*

Balakrishnan et al. Metalloprotease Inhibitors GM6001 and TAPI-0 Inhibit the Obligate Intracellular Human Pathogen *Chlamydia trachomatis* by Targeting Peptide Deformylase of the Bacterium. J. Biol. Chem. 281(24): 16691-16699, 2006.*

Bianchi et al., "Efficient Homolactic Fermentation by *Kluyveromyces lactis* Strains Defective in Pyruvate Utilization and Transformed with Heterologous LDH Gene" *Applied and Environmental Microbiology* 5621-5625 (Dec. 2001).

Waldvogel et al., "Structure and function of L-lactate dehydrogenases from thermophilic and mesophilic bacteria" *Biol. Chem. Hoppe Seyler* 368(10)1391-9 (Oct. 1987), Abstract Only.

Waldvogel et al., "*B.megaterium* L-lactate dehydrogenase gene" *NCBI Accession M22305* Apr. 1993, pp. 1-2.

Nosek et al., Genetic manipulation of the pathogenic yeast *Candida parosilosis*. Curr. Genet. Sep. 2002 42(1) abstract.

Kaiser et al., Pyruvate decarboxylase regulator: NCBI Accession CAA76590 May 1999, pp. 1-2.

Porro et al., "Development of Metabolically Engineered *Saccharomyces cerevisiau* Cells for the Porduction of Lactic Acid" *Biotechnol. Prog.* 11:294-298 (1995).

Schaaff et al., "A deletion of the PDC1 gene for pyruvate decarboxylase of yeast causes a different phenotype than previously isolated point mutations" *Curr Genet.* 15(2):75-81 (Feb. 1989), Abstract Only.

Kaiser et al., "Identification of a Gene Encoding the Pyruvate Decarboxylase Gene Regulator CaPdc2p from *Candida albicans*" *Yeast* 15:585-591 (1999).

Seeboth et al., "pdc1° Mutants of *Saccharomyces cerevisiae* Give Evidence for an Additonal Structural PDC Gene:Cloning of *PDC*5, a Gene Homologous to PDC1" *Journal of Bacteriology* 172(2) 678-685 (Feb. 1990).

Hohmann et al., "Characterization of PDC2, a gene necessary for high level expression of pyruvate decarboxylase structural genes in *Saccharomyces cerevisiae*" *Mol. Gen. Genet.* 241(5-6):657-66 (Dec. 1993), Abstract Only.

Wright et al., "Identification, cloning and characterization of a new gene required for full pyruvate decarboxylast activity in *Saccharomyces cerevisiae*" Curr Genet 15(3):171-5 (Mar. 1989), Abstract Only.

Bhowmik et al., "Cloning and overexpression of *Lactobacillus helveticus* D-lactate dehydrogenase gene in *Escherichia coli*" NBCI Accession No. P30901, No journal article; P30901 only.

* cited by examiner

*Primary Examiner*—Nancy Vogel
*Assistant Examiner*—Michele K. Joike
(74) *Attorney, Agent, or Firm*—Gary C Cohn PLC

(57) ABSTRACT

Recombinant yeast are provided having, in one aspect, multiple exogenous LDH genes integrated into the genome, while leaving native PDC genes intact. In a second aspect, recombinant yeast are provided having an exogenous LDH gene integrated into its genome at the locus of a native PDC gene, with deletion of the native PDC gene. The recombinant yeast are useful in fermentation process for producing lactic acid.

9 Claims, 19 Drawing Sheets

FIG. 1: General expression vectors pNC2
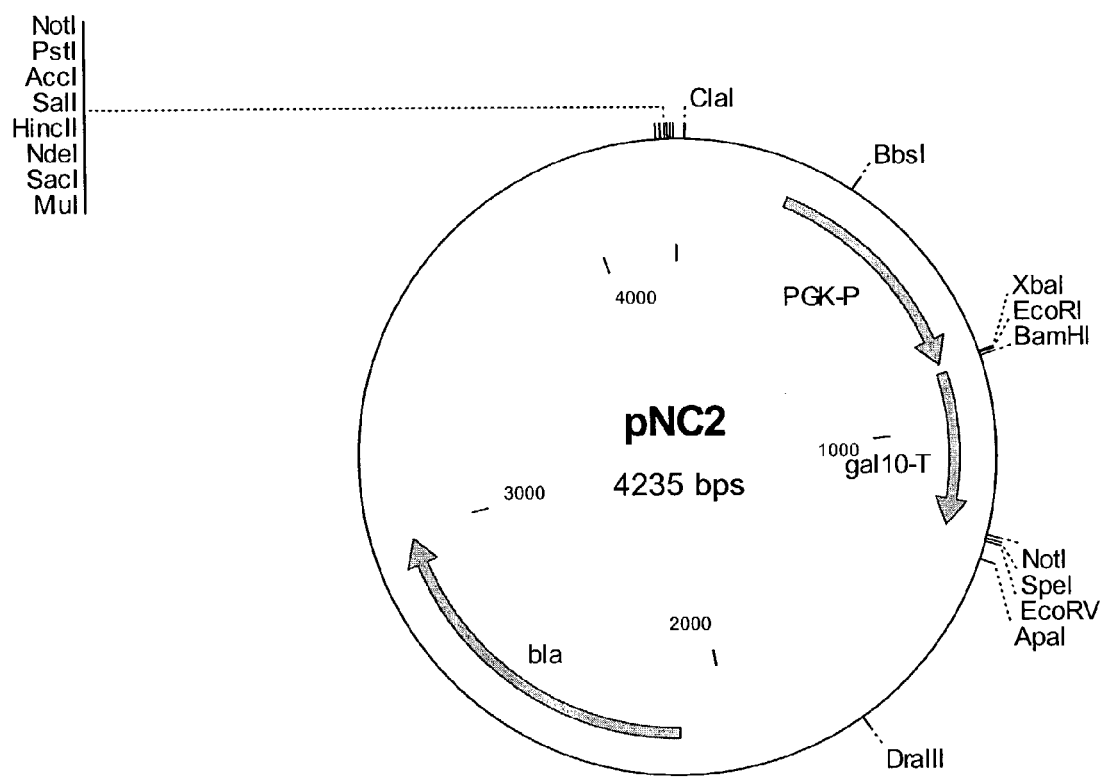

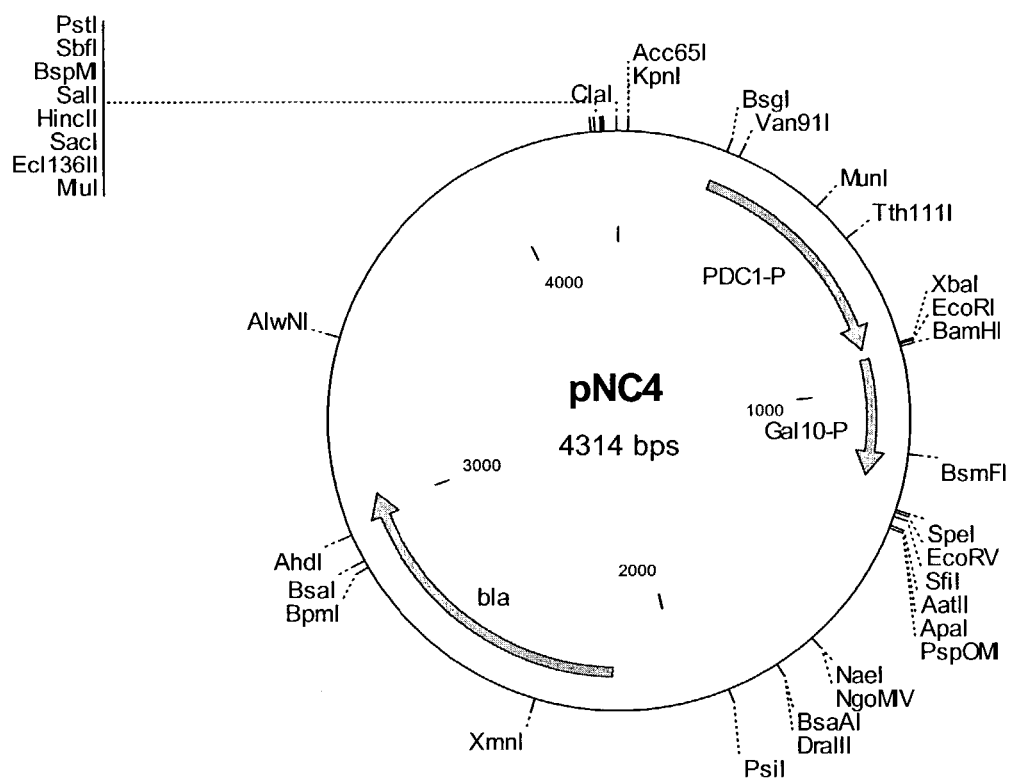
FIG. 2: General expression vector pNC4

FIG. 2a. 1.235 kbp NotI digested fragment that has the *Saccharomyces cerevisiae ScPGK1* promoter, multiple cloning site and the *ScGAL10* terminator for gene expression

```
5'- GGCCGCGGAT CGCTCTTCCG CTATCGATTA ATTTTTTTTT
CTTTCCTCTT TTTATTAACC TTAATTTTTA TTTTAGATTC CTGACTTCAA
CTCAAGACGC ACAGATATTA TAACATCTGC ACAATAGGCA TTTGCAAGAA
TTACTCGTGA GTAAGGAAAG AGTGAGGAAC TATCGCATAC CTGCATTTAA
AGATGCCGAT TTGGGCGCGA ATCCTTTATT TTGGCTTCAC CCTCATACTA
TTATCAGGGC CAGAAAAGG AAGTGTTTCC CTCCTTCTTG AATTGATGTT
ACCCTCATAA AGCACGTGGC CTCTTATCGA GAAAGAAATT ACCGTCGCTC
GTGATTTGTT TGCAAAAGA ACAAAACTGA AAAAACCCAG ACACGCTCGA
CTTCCTGTCT TCCTATTGAT TGCAGCTTCC AATTTCGTCA CACAACAAGG
TCCTAGCGAC GGCTCACAGG TTTTGTAACA AGCAATCGAA GGTTCTGGAA
TGGCGGGAAA GGGTTTAGTA CCACATGCTA TGATGCCCAC TGTGATCTCC
AGAGCAAAGT TCGTTCGATC GTACTGTTAC TCTCTCTCTT TCAAACAGAA
TTGTCCGAAT CGTGTGACAA CAACAGCCTG TTCTCACACA CTCTTTTCTT
CTAACCAAGG GGGTGGTTTA GTTTAGTAGA ACCTCGTGAA ACTTACATTT
ACATATATAT AAACTTGCAT AAATTGGTCA ATGCAAGAAA TACATATTTG
GTCTTTTCTA ATTCGTAGTT TTTCAAGTTC TTAGATGCTT TCTTTTTCTC
TTTTTTACAG ATCATCAAGG AAGTAATTAT CTACTTTTTA CAACAAATCT
AGAATTCGGA TCCGGTAGAT ACATTGATGC TATCAATCAA GAGAACTGGA
AAGATTGTGT AACCTTGAAA AACGGTGAAA CTTACGGGTC AAGACCCTC
TACAGATTTT CCTGATTTGC CAGCTTACTA TCCTTCTTGA AAATATGCAC
TCTATATCTT TTAGTTCTTA ATTGCAACAC ATAGATTTGC TGTATAACGA
ATTTTATGCT ATTTTTTAAA TTTGGAGTTC AGTGATAAAA GTGTCACAGC
GAATTTCCTC ACATGTAGGA CCGAATTGTT TACAAGTTCT CTGTACCACC
ATGGAGACAT CAAAGATTGA AAATCTATGG AAAGATATGG ACGGTAGCAA
CAAGAATATA GCACGAGCCG CGGATTTATT TCGTTACGCA TGCGC - 3'
```

FIG. 2b: NotI restriction fragment of a 1.3 kbp sequence comprising of the *S. cerevisiae* PDC1 promoter and *ScGAL10* terminator and a multiple cloning site between the terminator and promoter 5'- GGCCGCGGATCGCTCTTCCGCTATCGATAACAAGCTCATGCAAAG
AGGTGGTACCCGCACGCCGAAATGCATGCAAGTAACCTATTCAAAGTAAT
ATCTCATACATGTTTCATGAGGGTAACAACATGCGACTGGGTGAGCATAT
GTTCCGCTGATGTGATGTGCAAGATAAACAAGCAAGGCAGAAACTAACT
TCTTCTTCATGTAATAAACACACCCCGCGTTTATTTACCTATCTCTAAACT
TCAACACCTTATATCATAACTAATATTTCTTGAGATAAGCACACTGCACC
CATACCTTCCTTAAAAACGTAGCTTCCAGTTTTTGGTGGTTCCGGCTTCCT
TCCCGATTCCGCCCGCTAAACGCATATTTTGTTGCCTGGTGGCATTTGCA
AAATGCATAACCTATGCATTTAAAAGATTATGTATGCTCTTCTGACTTTTC
GTGTGATGAGGCTCGTGGAAAAAATGAATAATTTATGAATTTGAGAACAA
TTTTGTGTTGTTACGGTATTTACTATGGAATAATCAATCAATTGAGGATT
TTATGCAAATATCGTTTGAATATTTTCCGACCCTTTGAGTACTTTTCTTCA
TAATTGCATAATATTGTCCGCTGCCCTTTTCTGTTAGACGGTGTCTTGA
TCTACTTGCTATCGTTCAACACCACCTTATTTCTAACTATTTTTTTTTAG
CTCATTTGAATCAGCTTATGGTGATGGCACATTTTTGCATAAACCTAGCTG
TCCTCGTTGAACATAGGAAAAAAAAATATATAAACAAGGCTCTTTCACTC
TCCTTGCAATCAGATTTGGGTTTGTTCCCTTTATTTTCATATTTCTTGTCAT
ATTCCTTTCTCAATTATTATTTCTACTCATAACCTCACGCAAAATAACAC
AGTCAAATCTAGAATTCGGATCCGGTAGATACATTGATGCTATCAATCCA
GAGAACTGGAAAGATTGTGTAGCCTTGAAAAACGGTGAAACTTACGGGT
CCAAGATTGTCTACAGATTTTCCTGATTTGCCAGCTTACTATCCTTCTTGA
AAATATGCACTCTATATCTTTTAGTTCTTAATTGCAACACATAGATTTGCT
GTATAACGAATTTTATGCTATTTTTAAATTTGGAGTTCAGTGATAAAAGT
GTCACAGCGAATTTCCTCACATGTAGGGACCGAATTGTTTACAAGTTCTC
TGTACCACCATGGAGACATCAAAAATTGAAAATCTATGGAAAGATATGG
ACGGTAGCAACAAGAATATAGCACGAGCCGCGGATTTATTTCGTTACGCA
TGCGC – 3'

FIG. 3: Map of plasmid pVR22
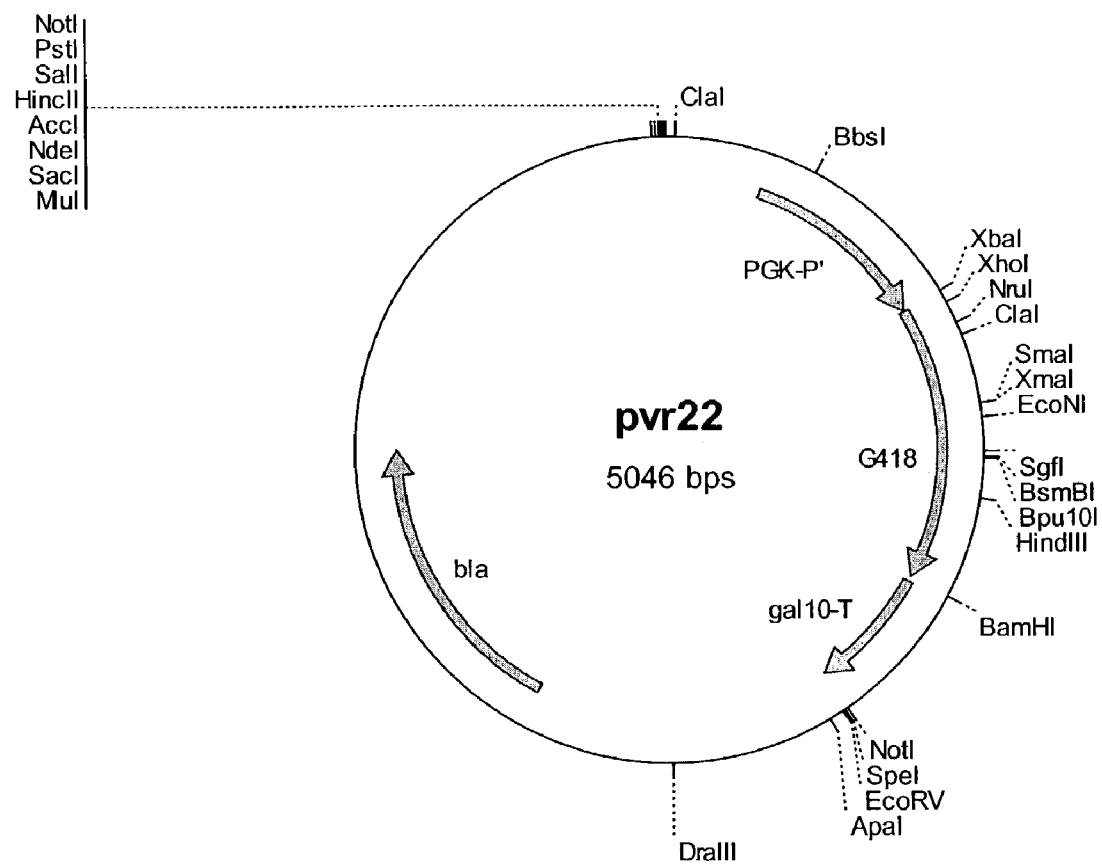

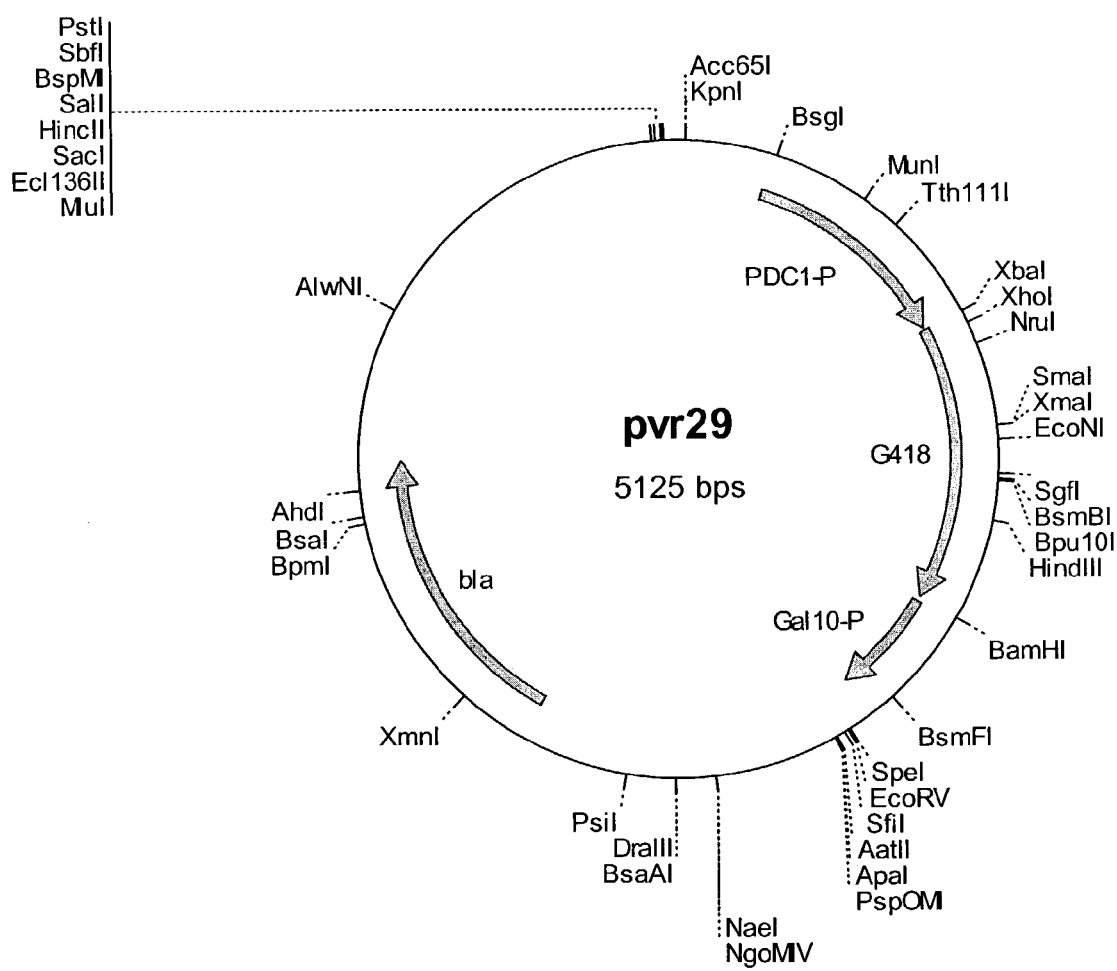
FIG. 4: Map of pVR29

FIG. 5: Construction of pPS9.
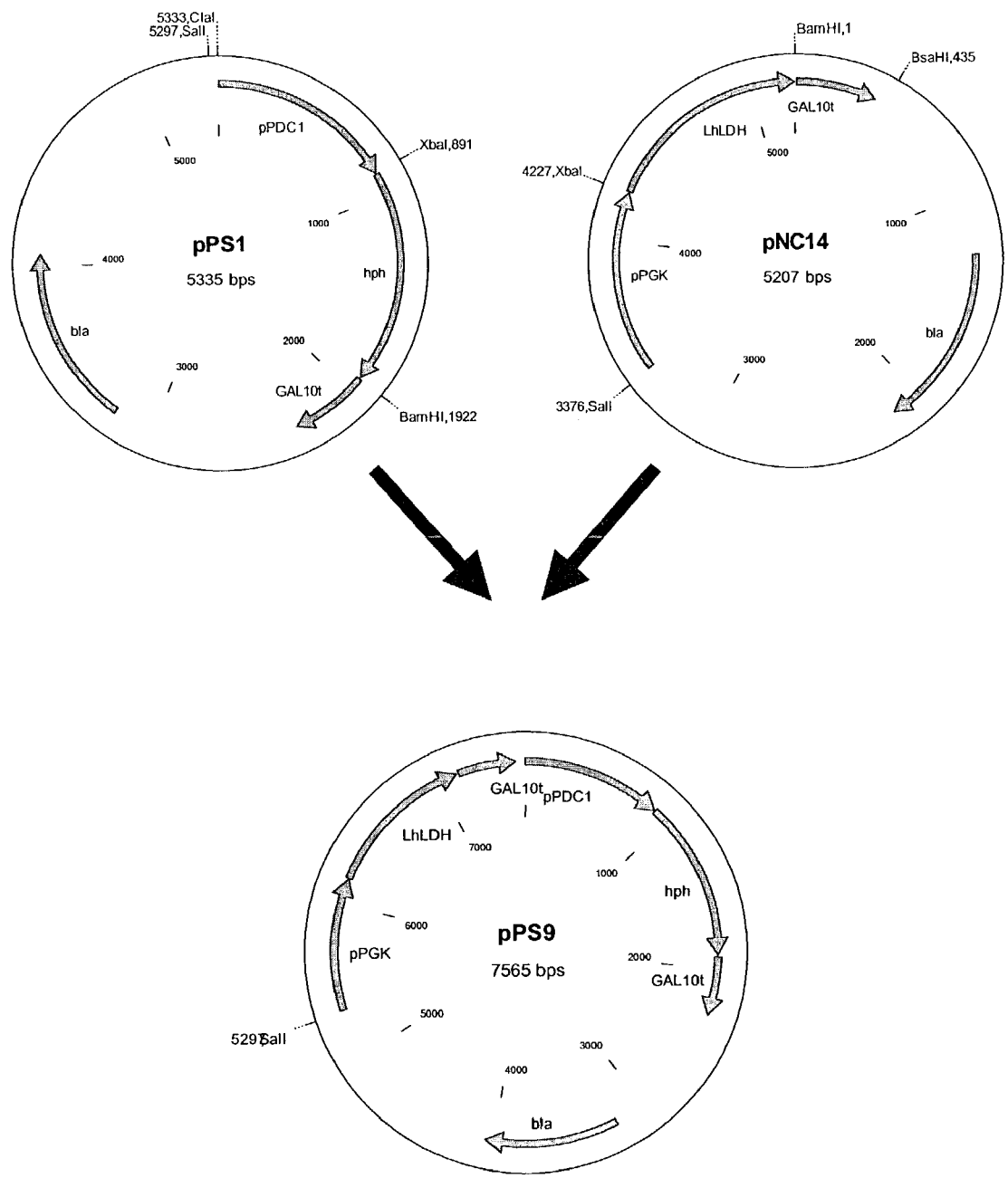

FIG. 6: Map of pVR39
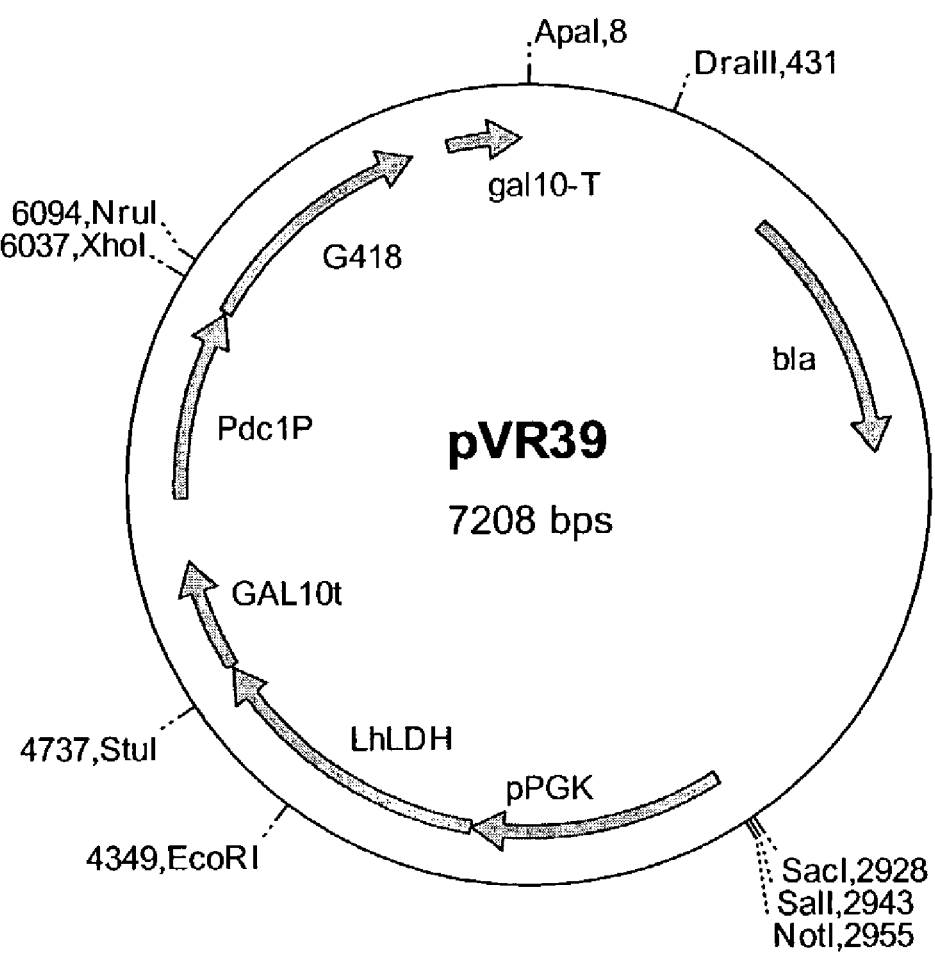

FIG. 7: Map of pVR1
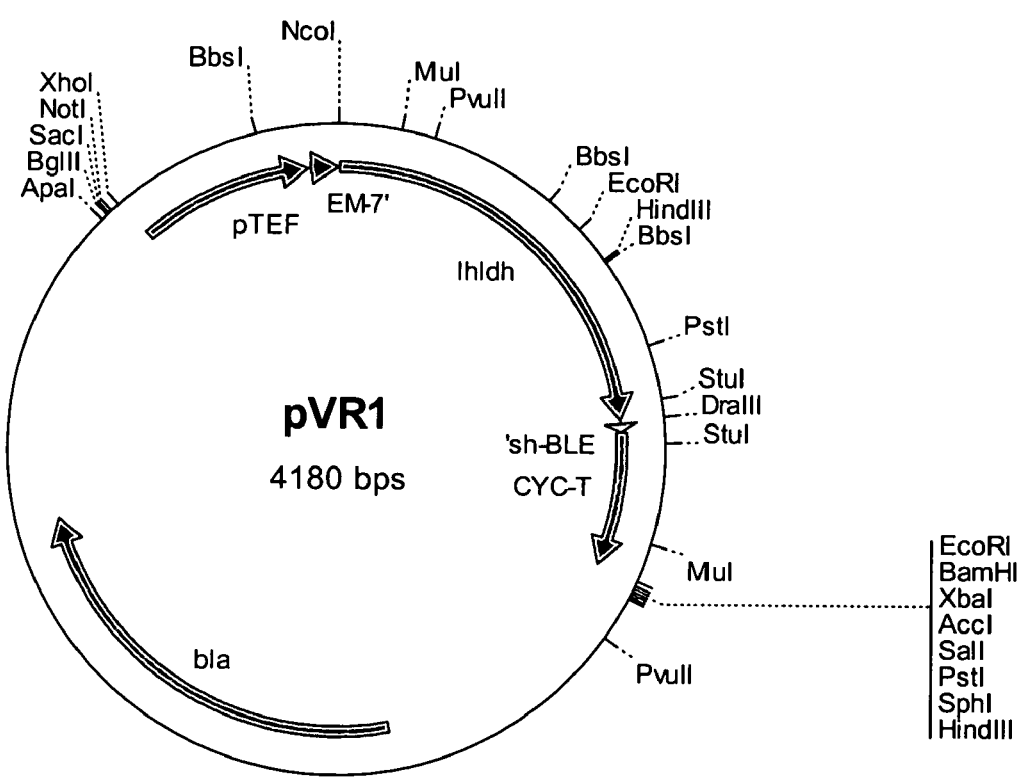

FIG. 8: Plasmid map of pSO18
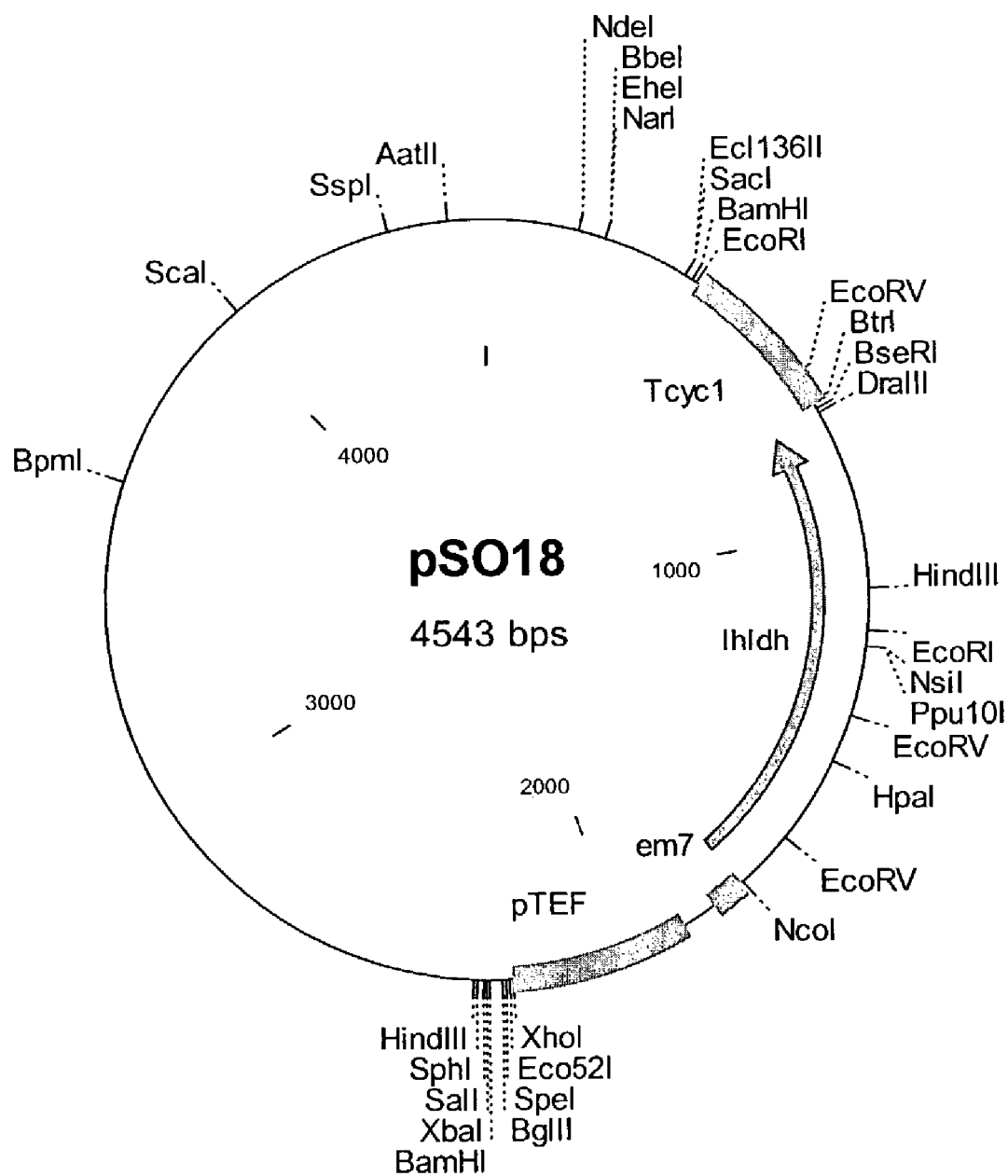

FIG. 9: Plasmid map of pSO19
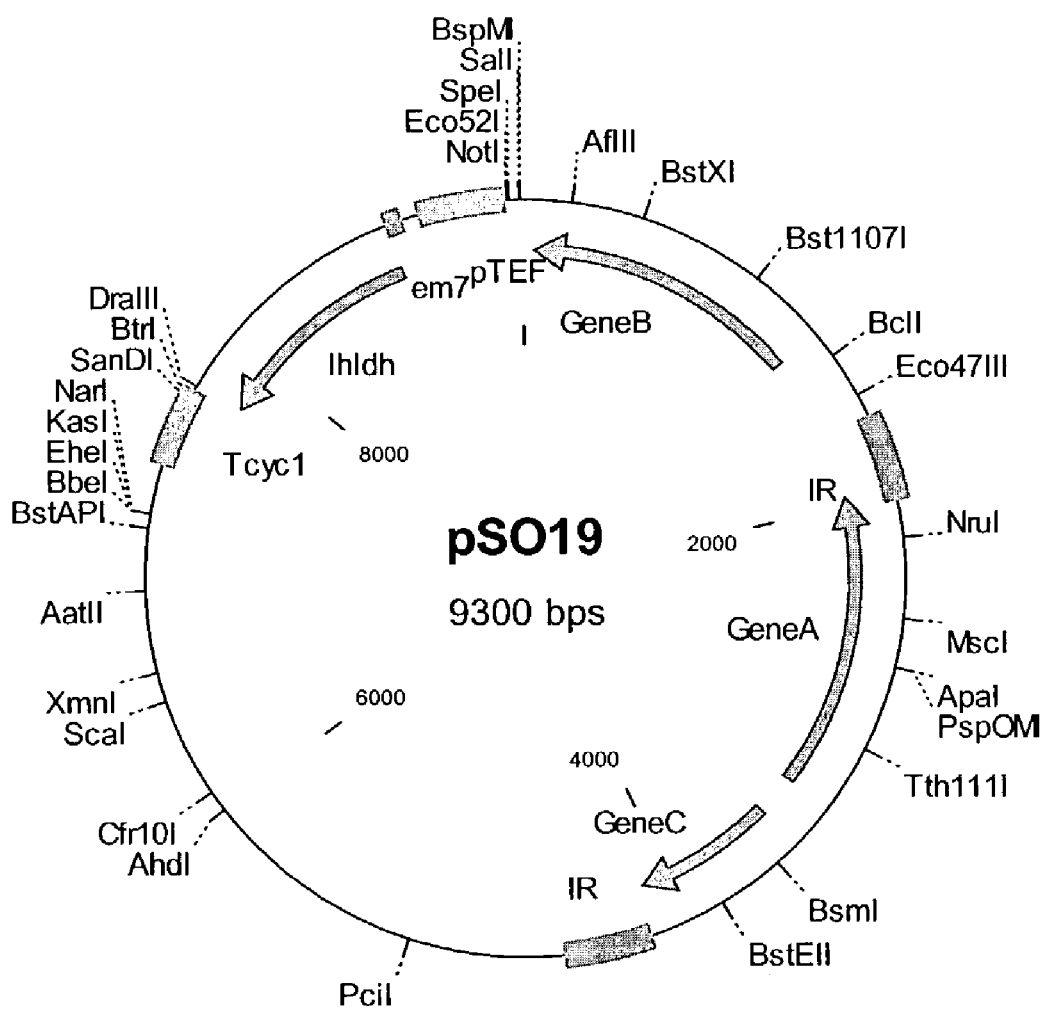

FIG. 10: Map of plasmid pSO20
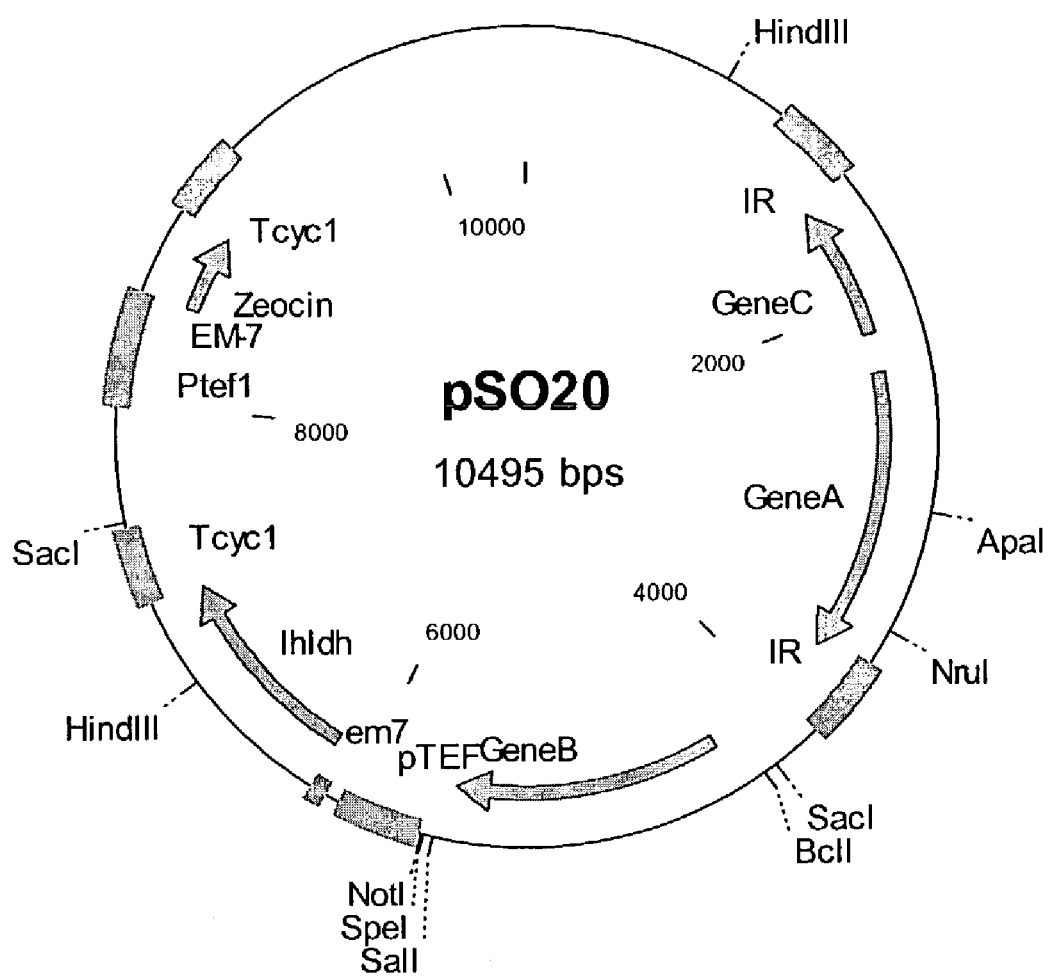

FIG. 11: Map of pVR41
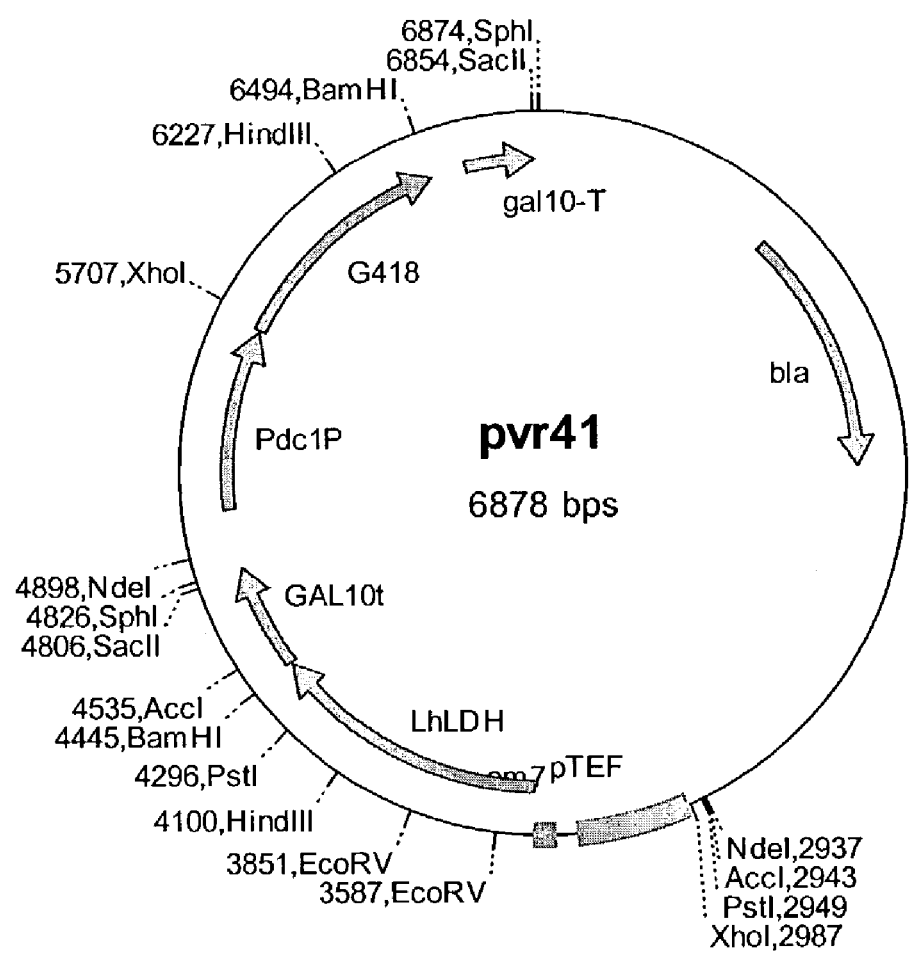

FIG. 12. Map of pVR24
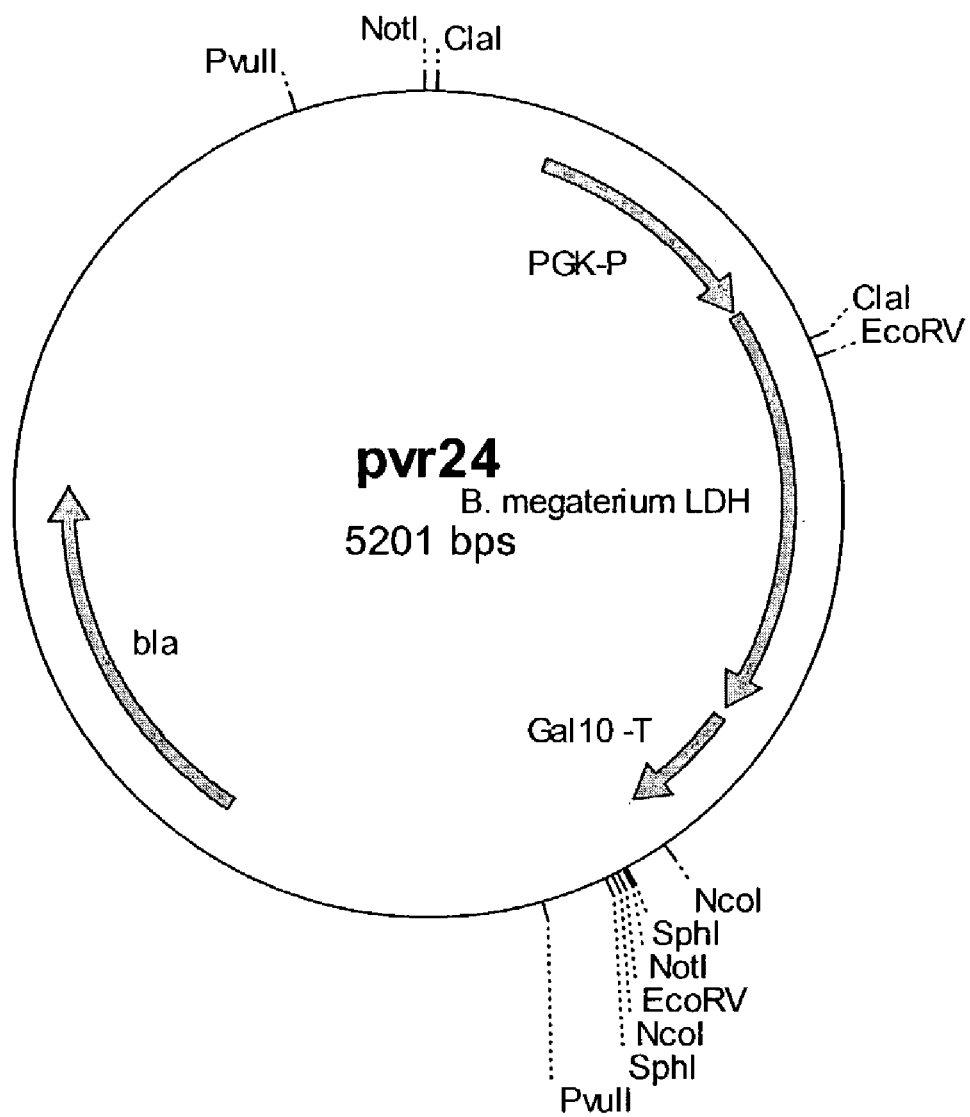

FIG. 13: pCA3 Plasmid Map
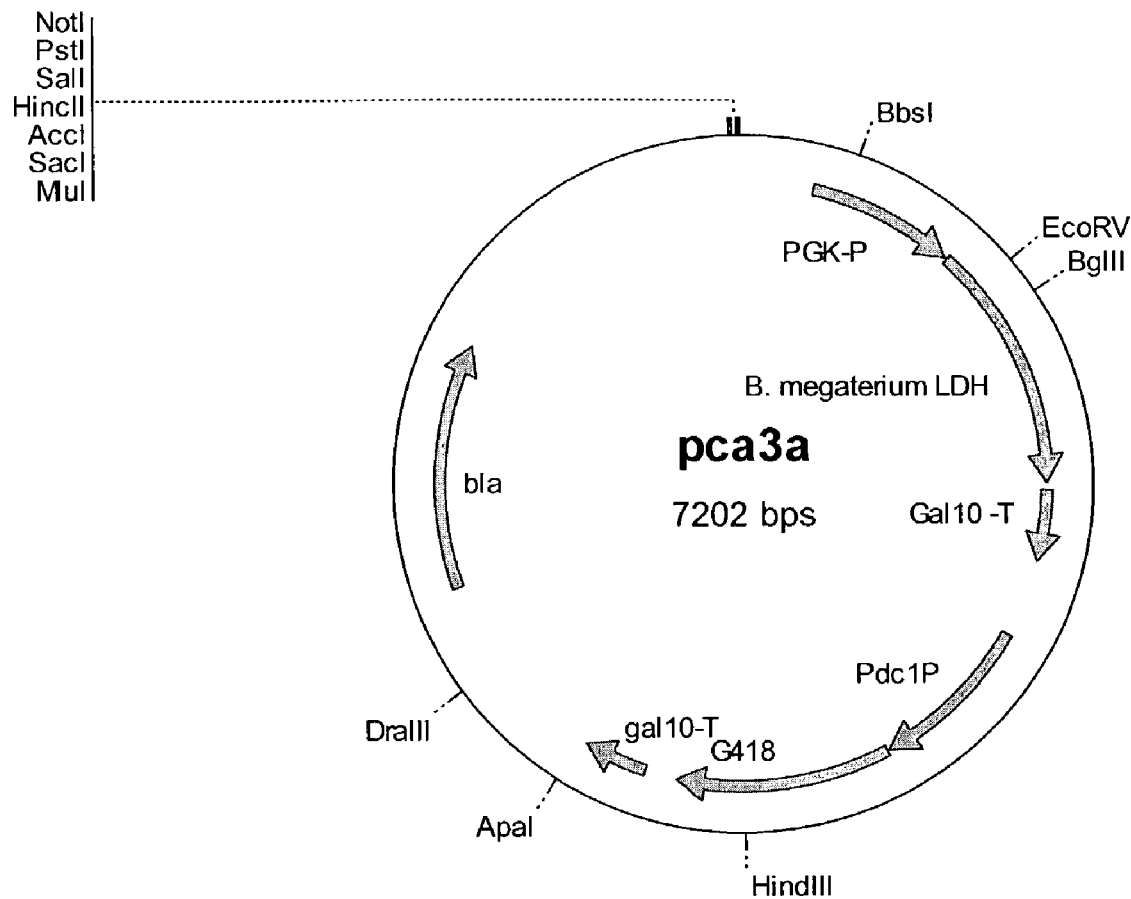

FIG. 14: Map of pVR38
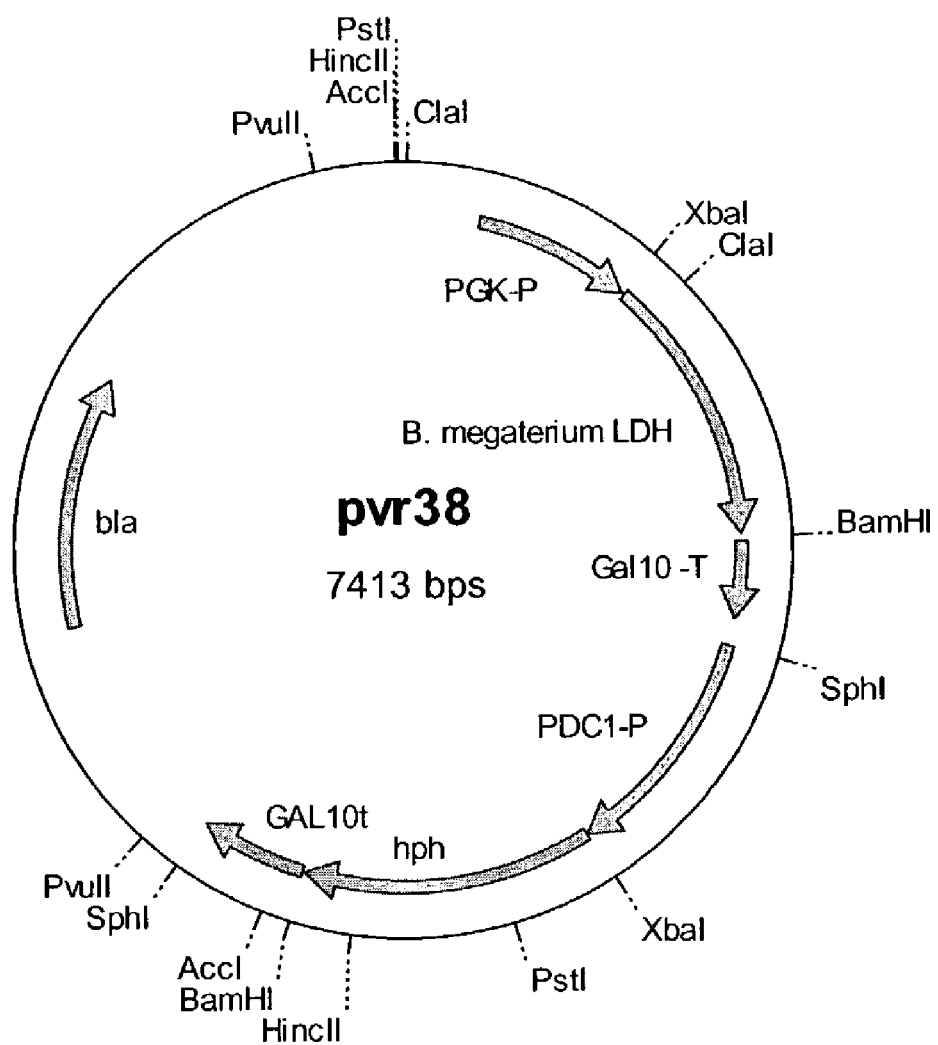

**Vector pBH5b for the targeted integration of DNA into the Pyruvate Decarboxylase 1 locus of *Kluyveromyces marxianus***
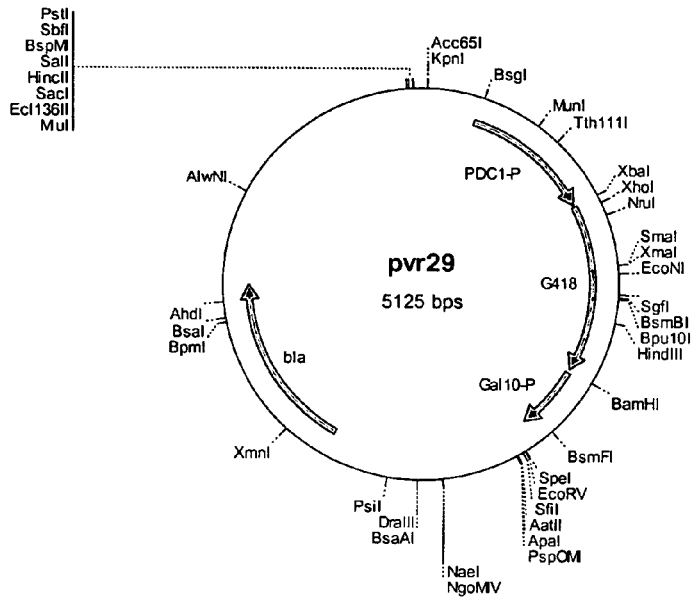
FIG. 15a
FIG. 15b
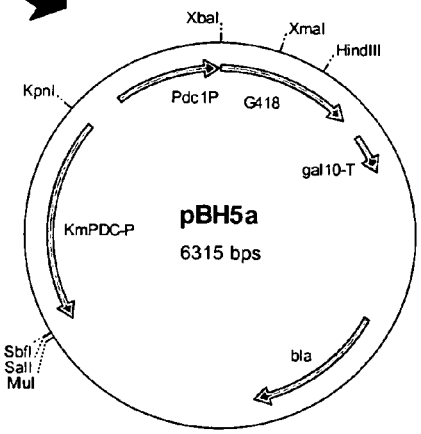
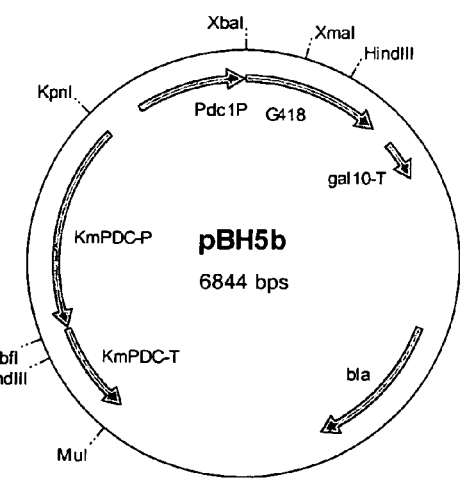
FIG. 15c FIG. 16: Vector pBH8 for the targeted integration of *Lh-L-LDH* into the *Pyruvate Decarboxylase 1* locus of *Kluyveromyces marxianus*
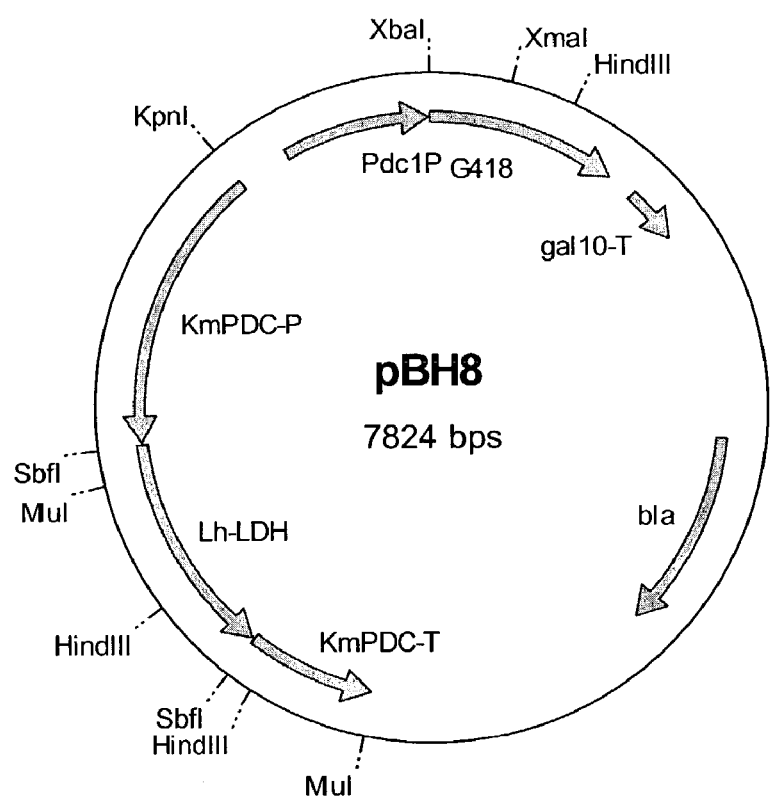

FIG 17A
Target Gene
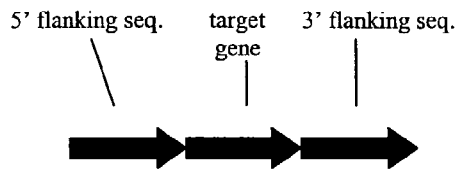
Vector
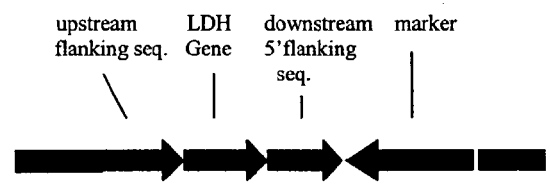
First Crossover
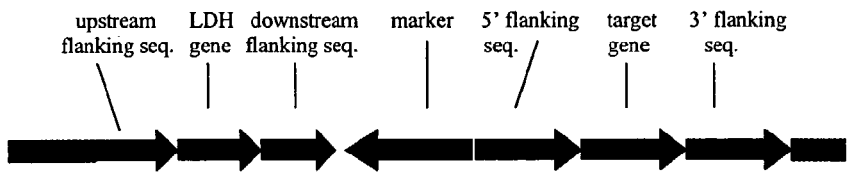
FIG 17B
Second Crossover Variations
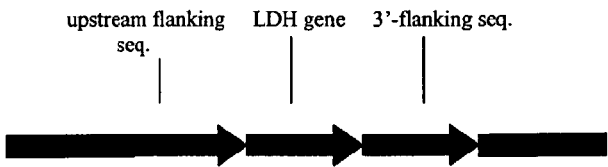
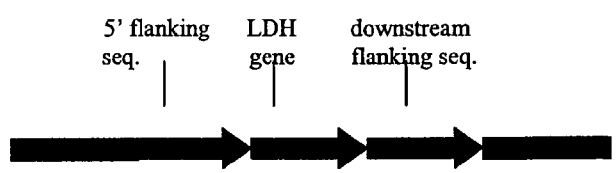

SEQUENCE LISTING

```
<160> NUMBER OF SEQ ID NOS: 38
<210> SEQ ID NO 1
<211> LENGTH: 848
<212> TYPE: DNA
<213> ORGANISM: Saccharomyces cerevisiae;

<400> SEQUENCE: 1
gcggccgcgg atcgctcttc cgctatcgat taatttttt ttctttcctc tttttattaa      60
ccttaatttt tattttagat tcctgacttc aactcaagac gcacagatat tataacatct     120
gcacaatagg catttgcaag aattactcgt gagtaaggaa agagtgagga actatcgcat     180
```

```
acctgcattt aaagatgccg atttgggcgc gaatcctttta ttttggcttc accctcatac    240
tattatcagg gccagaaaaa ggaagtgttt ccctccttct tgaattgatg ttaccctcat    300
aaagcacgtg gcctcttatc gagaaagaaa ttaccgtcgc tcgtgatttg tttgcaaaaa    360
gaacaaaact gaaaaaaccc agacacgctc gacttcctgt cttcctattg attgcagctt    420
ccaatttcgt cacacaacaa ggtcctagcg acggctcaca ggttttgtaa caagcaatcg    480
aaggttctgg aatggcggga aagggtttag taccacatgc tatgatgccc actgtgatct    540
ccagagcaaa gttcgttcga tcgtactgtt actctctctc tttcaaacag aattgtccga    600
atcgtgtgac aacaacagcc tgttctcaca cactctttct ttctaaccaa ggggatggtt    660
tagtttagta gaacctcgtg aaacttacat ttacatatat ataaacttgc ataaattggt    720
caatgcaaga aatacatatt tggtcttttc taattcgtag ttttttcaagt tcttagatgc    780 tttcttttc tcttttttac agatcatcaa ggaagtaatt atctactttt tacaacaaat    840
ctagaatt                                                              848

<210> SEQ ID NO 2
<211> LENGTH: 376
<212> TYPE: DNA
<213> ORGANISM: Saccharomyces cerevisiae;

<400> SEQUENCE: 2
gtagatacat tgatgctatc aatccagaga actggaaaga ttgtgtagcc ttgaaaaacg     60
gtgaaactta cgggtccaag attgtctaca gattttcctg atttgccagc ttactatcct    120
tcttgaaaat atgcactcta tatcttttag ttcttaattg caacacatag atttgctgta    180
taacgaattt tatgctattt tttaaatttg gagttcagtg ataaaagtgt cacagcgaat    240
ttcctcacat gtagggaccg aattgtttac aagttctctg taccaccatg gagacatcaa    300
aaattgaaaa tctatggaaa gatatggacg gtagcaacaa gaatatagca cgagccgcgg    360
atttatttcg ttacgc                                                     376

<210> SEQ ID NO 3
<211> LENGTH: 27
<212> TYPE: DNA
<213> ORGANISM: Artificial Sequence;
<220> FEATURE:
<223> OTHER INFORMATION: PSPDCS1 primer

<400> SEQUENCE: 3
ccatcgataa caagctcatg caaagag                                          27

<210> SEQ ID NO 4
<211> LENGTH: 28
<212> TYPE: DNA
<213> ORGANISM: Artificial Sequence;
<220> FEATURE:
<223> OTHER INFORMATION: PSPDCAS2 primer

<400> SEQUENCE: 4
gctctagatt tgactgtgtt attttgcg                                         28

<210> SEQ ID NO 5
<211> LENGTH: 30
<212> TYPE: DNA
<213> ORGANISM: Artificial Sequence;
<220> FEATURE:
<223> OTHER INFORMATION: 5'G fragment primer
```

```
<400> SEQUENCE: 5
gctctagatg agccatattc aacgggaaac                                30

<210> SEQ ID NO 6
<211> LENGTH: 30
<212> TYPE: DNA
<213> ORGANISM: Artificial Sequence;
<220> FEATURE:
<223> OTHER INFORMATION: 3'G fragment primer

<400> SEQUENCE: 6
atggatcctt agaaaaactc atcgagcatc                                30

<210> SEQ ID NO 7
<211> LENGTH: 29
<212> TYPE: DNA
<213> ORGANISM: Artificial Sequence;
<220> FEATURE:
<223> OTHER INFORMATION: 5'HYGXBA1 primer

<400> SEQUENCE: 7
aagctctaga tgaaaaagcc tgaactcac                                 29

<210> SEQ ID NO 8
<211> LENGTH: 29
<212> TYPE: DNA
<213> ORGANISM: Artificial Sequence;
<220> FEATURE:
<223> OTHER INFORMATION: 3'HYGBAMH1 primer

<400> SEQUENCE: 8
cgcggatccc tattcctttg ccctcggac                                 29

<210> SEQ ID NO 9
<211> LENGTH: 30
<212> TYPE: DNA
<213> ORGANISM: Artificial Sequence;
<220> FEATURE:
<223> OTHER INFORMATION: PS15S primer

<400> SEQUENCE: 9
gctctagaat tatggcaaga gaggaaaaac                                30

<210> SEQ ID NO 10
<211> LENGTH: 27
<212> TYPE: DNA
<213> ORGANISM: Artificial Sequence;
<220> FEATURE:
<223> OTHER INFORMATION: PS16AS primer

<400> SEQUENCE: 10
cgggatcctc attgacgaac cttaacg                                   27

<210> SEQ ID NO 11
<211> LENGTH: 92
<212> TYPE: DNA
<213> ORGANISM: Artificial Sequence;
<220> FEATURE:
<223> OTHER INFORMATION: fwd HES oligo

<400> SEQUENCE: 11
cccaagcttg aattccccgg gggatccctg cagggtacca cgcgtagatc tactagtgcg   60
gccgcctcga gtctagaggg cccaagcttg gg                                92
```

<210> SEQ ID NO 12
<211> LENGTH: 91
<212> TYPE: DNA
<213> ORGANISM: Artificial Sequence;
<220> FEATURE:
<223> OTHER INFORMATION: [SO1][CMA2] oligo

<400> SEQUENCE: 12

```
ccaagcttgg gccctctaga ctcgaggcgg ccgcactagt agatctacgc gtggtaccct    60
gcagggatcc cccggggaat tcaagcttgg g                                   91
```

<210> SEQ ID NO 13
<211> LENGTH: 31
<212> TYPE: DNA
<213> ORGANISM: Artificial Sequence;
<220> FEATURE:
<223> OTHER INFORMATION: SO22 primer

<400> SEQUENCE: 13

```
ccgggatcca tggcaagaga ggaaaaacct c                                   31
```

<210> SEQ ID NO 14
<211> LENGTH: 32
<212> TYPE: DNA
<213> ORGANISM: Artificial Sequence;
<220> FEATURE:
<223> OTHER INFORMATION: SO23 primer

<400> SEQUENCE: 14

```
ccaagatctt tattgacgaa ccttaacgcc ag                                  32
```

<210> SEQ ID NO 15
<211> LENGTH: 34
<212> TYPE: DNA
<213> ORGANISM: Artificial Sequence;
<220> FEATURE:
<223> OTHER INFORMATION: VR1 primer

<400> SEQUENCE: 15

```
atccatggca agtattacgg ataaggatca ccaa                                34
```

<210> SEQ ID NO 16
<211> LENGTH: 32
<212> TYPE: DNA
<213> ORGANISM: Artificial Sequence;
<220> FEATURE:
<223> OTHER INFORMATION: VR2 primer

<400> SEQUENCE: 16

```
atcacgaagt gtcacgtacg ggtttcgatg tc                                  32
```

<210> SEQ ID NO 17
<211> LENGTH: 25
<212> TYPE: DNA
<213> ORGANISM: Artificial Sequence;
<220> FEATURE:
<223> OTHER INFORMATION: VR146 primer

<400> SEQUENCE: 17

```
gctgactacc cagattgtaa ggatg                                          25
```

<210> SEQ ID NO 18
<211> LENGTH: 27
<212> TYPE: DNA
<213> ORGANISM: Artificial
<220> FEATURE:

-continued

```
<223> OTHER INFORMATION: VR143 primer

<400> SEQUENCE: 18
ctgccagcgc atcaacaata ttttcac                                              27

<210> SEQ ID NO 19
<211> LENGTH: 27
<212> TYPE: DNA
<213> ORGANISM: Artificial Sequence;
<220> FEATURE:
<223> OTHER INFORMATION: VR142 primer

<400> SEQUENCE: 19
ctgccagcgc atcaacaata ttttcac                                              27

<210> SEQ ID NO 20
<211> LENGTH: 21
<212> TYPE: DNA
<213> ORGANISM: Artificial Sequence;
<220> FEATURE:
<223> OTHER INFORMATION: BM1270 primer

<400> SEQUENCE: 20
cctgagtcca cgtcattatt c                                                    21

<210> SEQ ID NO 21
<211> LENGTH: 22
<212> TYPE: DNA
<213> ORGANISM: Artificial Sequence;
<220> FEATURE:
<223> OTHER INFORMATION: BM179 primer

<400> SEQUENCE: 21
tgaagctatt tattcttgtt ac                                                   22

<210> SEQ ID NO 22
<211> LENGTH: 27
<212> TYPE: DNA
<213> ORGANISM: Artificial Sequence;
<220> FEATURE:
<223> OTHER INFORMATION: Bmeg5' primer

<400> SEQUENCE: 22
gctctagatg aaaacacaat ttacacc                                              27

<210> SEQ ID NO 23
<211> LENGTH: 28
<212> TYPE: DNA
<213> ORGANISM: Artificial Sequence;
<220> FEATURE:
<223> OTHER INFORMATION: Bmeg3' primer

<400> SEQUENCE: 23
atggatcctt acacaaaagc tctgtcgc                                             28

<210> SEQ ID NO 24
<211> LENGTH: 28
<212> TYPE: DNA
<213> ORGANISM: Artificial Sequence;
<220> FEATURE:
<223> OTHER INFORMATION: G5' primer

<400> SEQUENCE: 24
aaatctagat gagccatatt caacggga                                             28
```

<210> SEQ ID NO 25
<211> LENGTH: 29
<212> TYPE: DNA
<213> ORGANISM: Artificial Sequence;
<220> FEATURE:
<223> OTHER INFORMATION: G3' primer

<400> SEQUENCE: 25
ccggatcctt agaaaaactc atcgagcat                                29

<210> SEQ ID NO 26
<211> LENGTH: 27
<212> TYPE: DNA
<213> ORGANISM: Artificial Sequence;
<220> FEATURE:
<223> OTHER INFORMATION: BmLDH3 primer

<400> SEQUENCE: 26
gtacgcatta ccaaggctat tttagat                                  27

<210> SEQ ID NO 27
<211> LENGTH: 30
<212> TYPE: DNA
<213> ORGANISM: Artificial Sequence;
<220> FEATURE:
<223> OTHER INFORMATION: 5'-Flank 5' primer

<400> SEQUENCE: 27
caagaaggta ccctctctcta aacttgaaca                              30

<210> SEQ ID NO 28
<211> LENGTH: 32
<212> TYPE: DNA
<213> ORGANISM: Artificial Sequence;
<220> FEATURE:
<223> OTHER INFORMATION: 5'-Flank 3' primer

<400> SEQUENCE: 28
gtaattcctg caggtgcaat tatttggttt gg                            32

<210> SEQ ID NO 29
<211> LENGTH: 32
<212> TYPE: DNA
<213> ORGANISM: Artificial Sequence;
<220> FEATURE:
<223> OTHER INFORMATION: 3'-Flank 5' primer

<400> SEQUENCE: 29
ccaagccctg caggagaggg agaggataaa ga                            32

<210> SEQ ID NO 30
<211> LENGTH: 30
<212> TYPE: DNA
<213> ORGANISM: Artificial Sequence;
<220> FEATURE:
<223> OTHER INFORMATION: 3'-Flank 3' primer

<400> SEQUENCE: 30
ctcgtaacgc gtgtacaagt tgtggaacaa                               30

<210> SEQ ID NO 31
<211> LENGTH: 32
<212> TYPE: DNA
<213> ORGANISM: Artificial Sequence;
<220> FEATURE:
<223> OTHER INFORMATION: 1-LDH 5' primer

```
<400> SEQUENCE: 31
acaaatcctg caggatggca agagaggaaa aa                              32

<210> SEQ ID NO 32
<211> LENGTH: 32
<212> TYPE: DNA
<213> ORGANISM: Artificial Sequence;
<220> FEATURE:
<223> OTHER INFORMATION: 1-LDH 3' primer

<400> SEQUENCE: 32
tatctacctg caggtcattg acgaacctta ac                              32

<210> SEQ ID NO 33
<211> LENGTH: 21
<212> TYPE: DNA
<213> ORGANISM: Artificial Sequence;
<220> FEATURE:
<223> OTHER INFORMATION: PDC1 primer

<400> SEQUENCE: 33
aagcaccaag gccttcaaca g                                          21

<210> SEQ ID NO 34
<211> LENGTH: 21
<212> TYPE: DNA
<213> ORGANISM: Artificial Sequence;
<220> FEATURE:
<223> OTHER INFORMATION: 1-LDH 3' primer

<400> SEQUENCE: 34
tcgatatcgc taaggaacgc g                                          21

<210> SEQ ID NO 35
<211> LENGTH: 21
<212> TYPE: DNA
<213> ORGANISM: Artificial Sequence;
<220> FEATURE:
<223> OTHER INFORMATION: PDC1 5' primer

<400> SEQUENCE: 35
cgcaaagaaa agctccacac c                                          21

<210> SEQ ID NO 36
<211> LENGTH: 21
<212> TYPE: DNA
<213> ORGANISM: Artificial Sequence;
<220> FEATURE:
<223> OTHER INFORMATION: PDC1 3' primer

<400> SEQUENCE: 36
cccatacgct tataatcccc c                                          21

<210> SEQ ID NO 37
<211> LENGTH: 1235
<212> TYPE: DNA
<213> ORGANISM: Saccharomyces cerevisiae;

<400> SEQUENCE: 37
ggccgcggat cgctcttccg ctatcgatta attttttttt ctttcctctt tttattaacc    60 ttaatttta ttttagattc ctgacttcaa ctcaagacgc acagatatta taacatctgc    120
acaataggca tttgcaagaa ttactcgtga gtaaggaaag agtgaggaac tatcgcatac    180
ctgcatttaa agatgccgat ttgggcgcga atcctttatt ttggcttcac cctcatacta    240
```

```
ttatcagggc cagaaaaagg aagtgtttcc ctccttcttg aattgatgtt accctcataa         300
agcacgtggc ctcttatcga gaaagaaatt accgtcgctc gtgatttgtt tgcaaaaaga         360
acaaaactga aaaacccag acacgctcga cttcctgtct tcctattgat tgcagcttcc          420
aatttcgtca cacaacaagg tcctagcgac ggctcacagg ttttgtaaca agcaatcgaa         480
ggttctggaa tggcgggaaa gggtttagta ccacatgcta tgatgcccac tgtgatctcc        540
agagcaaagt tcgttcgatc gtactgttac tctctctctt tcaaacagaa ttgtccgaat         600
cgtgtgacaa caacagcctg ttctcacaca ctcttttctt ctaaccaagg gggtggttta         660
gtttagtaga acctcgtgaa acttacattt acatatatat aaacttgcat aaattggtca         720
atgcaagaaa tacatatttg gtcttttcta attcgtagtt tttcaagttc ttagatgctt         780 tcttttctc ttttttacag atcatcaagg aagtaattat ctactttta caacaaatct           840 agaattcgga tccggtagat acattgatgc tatcaatcaa gagaactgga agattgtgt          900 aaccttgaaa aacggtgaaa cttacgggtc caagaccctc tacagatttt cctgatttgc        960
cagcttacta tccttcttga aaatatgcac tctatatctt ttagttctta attgcaacac        1020
atagatttgc tgtataacga attttatgct attttttaaa tttggagttc agtgataaaa        1080
gtgtcacagc gaatttcctc acatgtagga ccgaattgtt tacaagttct ctgtaccacc        1140
atggagacat caaagattga aaatctatgg aaagatatgg acggtagcaa caagaatata       1200
gcacgagccg cggatttatt tcgttacgca tgcgc                                   1235

<210> SEQ ID NO 38
<211> LENGTH: 1314
<212> TYPE: DNA
<213> ORGANISM: Saccharomyces cerevisiae;

<400> SEQUENCE: 38
ggccgcggat cgctcttccg ctatcgataa caagctcatg caaagaggtg gtacccgcac           60
gccgaaatgc atgcaagtaa cctattcaaa gtaatatctc atacatgttt catgagggta         120
acaacatgcg actgggtgag catatgttcc gctgatgtga tgtgcaagat aaacaagcaa         180
ggcagaaact aacttcttct tcatgtaata aacacacccc gcgtttattt acctatctct         240
aaacttcaac accttatatc ataactaata tttcttgaga taagcacact gcacccatac         300
cttccttaaa aacgtagctt ccagtttttg gtggttccgg cttccttccc gattccgccc         360
gctaaacgca tattttgtt gcctggtggc atttgcaaaa tgcataacct atgcatttaa          420
aagattatgt atgctcttct gacttttcgt gtgatgaggc tcgtggaaaa atgaataat          480 ttatgaattt gagaacaatt ttgtgttgtt acggtatttt actatggaat aatcaatcaa        540
ttgaggattt tatgcaaata tcgtttgaat attttttcga ccctttgagt acttttcttc       600
ataattgcat aatattgtcc gctgccccctt tttctgttag acggtgtctt gatctacttg       660
ctatcgttca acaccaccctt atttttctaac tattttttttt ttagctcatt tgaatcagct   720
tatggtgatg gcacatttttt gcataaacct agctgtcctc gttgaacata ggaaaaaaaa     780
atatataaac aaggctcttt cactctcctt gcaatcagat ttgggtttgt tcccttttatt      840 ttcatatttc ttgtcatatt cctttctcaa ttattatttt ctactcataa cctcacgcaa       900
aataacacag tcaaatctag aattcggatc cggtagatac attgatgcta tcaatccaga       960
gaactggaaa gattgtgtag ccttgaaaaa cggtgaaact tacgggtcca agattgtcta      1020
cagattttcc tgatttgcca gcttactatc cttcttgaaa atatgcactc tatatctttt      1080
```

| | | | | |
|---|---|---|---|---|
| agttcttaat | tgcaacacat | agatttgctg | tataacgaat | tttatgctat ttttttaaatt | 1140 |
| tggagttcag | tgataaaagt | gtcacagcga | atttcctcac | atgtagggac cgaattgttt | 1200 |
| acaagttctc | tgtaccacca | tggagacatc | aaaaattgaa | aatctatgga aagatatgga | 1260 |
| cggtagcaac | aagaatatag | cacgagccgc | ggatttattt | cgttacgcat gcgc | 1314 |

METHODS AND MATERIALS FOR THE PRODUCTION OF L-LACTIC ACID IN YEAST

This application claims priority to U.S. Provisional application No. 60/384,333, filed May 30, 2002.

This invention was made with U.S. Government support under Contract No. DE-FC-36-00GO10598, awarded by the Department of Energy. The U.S. government has certain rights in this invention.

BACKGROUND OF THE INVENTION

Lactic acid has wide industrial applicability including uses in chemical processing and synthesis, cosmetics, pharmaceuticals, plastics, and food production. Most industrial scale processes for making lactic acid are fermentation processes. Various lactic acid-producing bacteria have been used in those fermentation processes.

Recent research has investigated the use of recombinant yeast strains in lactic acid fermentation processes. Recombinant yeast potentially can provide several advantages over bacterial fermentations. Some yeast strains are more resistant to higher temperatures. This potentially allows for higher temperature fermentations, which can translate to faster rates of fermentations. Better resistance to high temperature can make it easier to purge a fermentation medium of contaminating microbes, as the medium can simply be heated to a temperature that the desired species can tolerate but at which the unwanted species die off. Lactic acid-producing bacteria such as *Lactobacilli* require a complex fermentation medium in order to produce efficiently. The complexity of the fermentation medium increases raw material costs and makes it more difficult and expensive to separate the lactic acid from the medium. Using recombinant yeast offers the possibility of reducing costs by using a simplified fermentation medium.

In addition, some yeast strains are more tolerant of reduced pH conditions that are lactic acid-producing bacteria. This is potentially a very important characteristic, as the pH of the fermentation medium will naturally drop as lactic acid is produced. In conventional processes, it is necessary to buffer the medium to a pH of about 5-8 with a base such as calcium hydroxide or calcium carbonate. This neutralizes the acid to form a lactate salt. This lactate salt must be split in a subsequent step to recover the lactate in the desired acid form. The need to buffer the fermentation medium therefore leads to significant additional costs for added raw materials (buffering agents and typically sulfuric acid to split the lactate salt), additional processing steps (to regenerate the free acid) and disposal of wastes (most often calcium carbonate that is generated in the salt-splitting step). These expenses can be reduced significantly if the fermentation can be conducted at reduced pH. The successful development of a lactic acid-producing strain that can tolerate reduced pH media is therefore greatly desirable.

Porro and coworkers have attempted to engineer a lactic-acid producing yeast by inserting an exogenous LDH (lactate dehydrogenase) gene into yeast cells from the species *S. cerevisiae, K. lactic, T. delbrueckii* and *Z. bailii,* and disrupting the cell's natural pyruvate pathway. See Porro et al., "Development of metabolically engineered *Saccharomyces cerevisiae* cells for the production of lactic acid", *Biotechnol. Prog.* 1995 May-June; 11(3): 294-8; Porro et al., "Replacement of a metabolic pathway for large-scale production of lactic acid from engineered yeasts", *App. Environ. Microbiol.* 1999 September:65(9):4211-5; Bianchi et al., "Efficient homolactic fermentation by *Kluyveromyces lactis* strains defective in pyruvate utilization and transformed with the heterologous LDH gene", *App. Environ. Microbiol.* 2001 December; 67(12)5621-5. Porro was able to produce a recombinant yeast that produces lactic acid, but the strains did not perform nearly well enough for implementation in a commercial process. To qualify for use in an industrial environment, the strain must generate good yields of lactic acid (i.e., high conversion of the substrate to lactic acid) and high productivity (i.e., rapid metabolism of the substrate to lactic acid). The yeast preferably is able to tolerate a medium having a high titer of lactic acid.

More recently, Rajgarhia and coworkers have created recombinant yeast that exhibit higher yields and productivities than those of Porro. See, for example, WO 00/71738, WO 02/42471 and PCT/US02/16223. However, it is desirable to provide a recombinant yeast in which yields and/or productivities are even further improved. In particular, it is desirable to provide a recombinant yeast strain that produces lactic acid at good yields and productivities under the anaerobic and/or microaerobic conditions that favor lactic acid production.

SUMMARY OF THE INVENTION

In one aspect, this invention is a process for integrating an exogenous lactate dehydrogenase gene into a yeast cell, wherein prior to the integration the cell has a targeted gene at a locus in its genome, the process comprising the steps of (a) transforming the cell with a recombinant nucleic acid comprising a lactate dehydrogenase (LDH) gene, flanking sequences upstream (i.e., 5') and downstream (i.e., 3') of the LDH gene, and at least one selection marker gene, said flanking sequences being homologous to flanking sequences upstream and downstream of the targeted gene, wherein the LDH gene is inserted into the genome of the cell adjacent to the locus of the targeted gene, (b) obtaining first transformed cells containing the LDH gene and the selection marker gene by growing the transformed cells in the presence of a selection agent, (c) growing said first transformed cells in nonselective media and (d) obtaining from said first transformed cells second transformed cells that contain the LDH gene but have deleted the selection marker gene and the targeted gene In preferred yeast cells, the targeted gene is advantageously pyruvate decarboxylase (PDC), alcohol dehydrogenase (ADH), orotidine-5'-phosphate decarboxylase (ura3), and 3-isopropylmalate dehydrogenase (leu2).

In this aspect of the invention, deletion of the selection marker gene and targeted gene occurs spontaneously within some proportion of the first transformed cells. As a result, the inserted LDH is operatively linked to functional promoter and terminator sequences that are homologous to the promoter and terminator sequences of the targeted gene.

A second aspect of this invention is a recombinant nucleic acid for transforming a cell of a yeast species, comprising at least one selection marker and an LDH gene that is exogenous to the yeast species, linked to flanking sequences upstream (5') and downstream (3') of the LDH gene, said flanking sequences being homologous to upstream and downstream, respectively, flanking sequences of a gene that is native to the yeast species.

A third aspect of the invention is a recombinant cell of a yeast species, wherein the yeast species contains a native targeted gene at a locus in its genome. The recombinant cell has an exogenous lactase dehydrogenase (LDH) gene integrated into its genome at the site of the targeted gene, and the targeted gene is deleted. The integrated LDH gene is operatively linked to functional promoter and terminator sequences homologous to those of the targeted gene. Such recombinant yeast cells exhibit unexpectedly high yields of lactic acid from carbohydrate substrates, together with high productivities, when used in a fermentation process. The recombinant cell also can produce lactic acid to high titers. Although the invention is not limited to any theory, it is believed that the insertion of the LDH gene at the locus of a native gene, together with the use of the native promoters and terminators as described herein, permits the cell to use existing gene regulation systems in connection with the functioning of the inserted LDH gene. This is believed to strongly favor the metabolic pathway to lactic acid when the cell experiences anaerobic or microaerobic fermentation conditions. Accordingly, a fourth aspect of this invention is a method for fermenting a carbohydrate to lactic acid comprising culturing the resulting cell under fermentation conditions in a medium containing a carbohydrate that is fermentable by the cell.

A fifth aspect of the invention is a cell of the species *K. marxianus* having multiple exogenous lactate dehydrogenase genes integrated into its genome, each under the control of functional promoter and terminator sequences, wherein the genome of the *K. marxianus* cell further contains a functional pyruvate decarboxylase gene. Surprisingly, excellent productivities and yields to lactic acid are obtained with this cell, together with surprisingly low yields to ethanol, even under low pH fermentation conditions. Again without limiting the invention to any theory, it is believed that by leaving the PDC pathway intact, the cell is better able to use its existing metabolic pathways to keep its metabolic processes in balance, promoting the overall health and vitality of the cell. Accordingly, a sixth aspect of the invention is a method for fermenting a carbohydrate to lactic acid comprising culturing the resulting cell under fermentation conditions in a medium containing a carbohydrate that is fermentable by the cell.

Specific preferred embodiments of the present invention will become evident from the following more detailed description of certain preferred embodiments and the claims.

BRIEF DESCRIPTION OF THE DRAWINGS

FIG. 1 is a diagram depicting the pNC2 plasmid.

FIG. 2 is a diagram depicting the pNC4 plasmid.

FIG. 2a is the nucleotide sequence (SEQ ID NO 37) of the 1.235 kbp NotI digested fragment that Has the *Saccharomyces cerevisiae* ScPGK1 promoter, multiple cloning site and the ScGAL10 terminator for gene expression.

FIG. 2b is the nucleotide sequence (SEQ ID NO. 38) of the NotI restriction fragment of a 1.3 kbp sequence comprising of the *S. cerevisiae* PDC1 promoter and ScGAL10 terminator and a multiple cloning site between the terminator and promoter.

FIG. 3 is a diagram depicting the pVR22 plasmid.

FIG. 4 is a diagram depicting the pVR29 plasmid.

FIG. 5 is a diagram depicting construction of the pPS9 plasmid from the pPS1 plasmid and the pNC14 plasmid FIG. 6 is a diagram depicting the pVR39 plasmid containing the *L. helveticus* L-LDH gene and the G418 resistance marker.

FIG. 7 is a diagram depicting the pVR1 plasmid containing the *L. helveticus* L-LDH-encoding gene sequence, the *S. cerevisiae* pTEF1 promoter and the *E. coli* EM7 promoter.

FIG. 8 is a diagram depicting the pSO18 plasmid.

FIG. 9 is a diagram depicting the pSO19 plasmid.

FIG. 10 is a diagram depicting the pSO20 plasmid.

FIG. 11 is a diagram depicting the pVR41 plasmid containing the *L. helveticus* L-LDH gene and the G418 resistance marker.

FIG. 12 is a diagram depicting the pCA3 plasmid containing the *B. megaterium* L-LDH gene and the G418 selection marker.

FIG. 13 is a diagram depicting the pVR24 plasmid.

FIG. 14 is a diagram depicting the pVR38 plasmid containing the *B. megaterium* L-LDH gene and the hygromycin resistance gene.

FIG. 15a is a diagram depicting construction of the pBH5a plasmids.

FIG. 15b is a diagram depicting construction of the pBH5a plasmids.

FIG. 15c is a diagram depicting construction of the pBH5b plasmid from the pVR29 and pBH5a plasmids.

FIG. 16 is a diagram depicting the pBH8 plasmid.

FIGS. 17A and 17B are schematic diagrams of genetic events that may be involved in targeted integration of exogenous LDH genes into a yeast chromosome according to an aspect of the invention.

DETAILED DESCRIPTION OF THE INVENTION

In the first two aspects of the invention, an exogenous LDH gene is integrated into the genome in a yeast cell at the locus of a targeted native gene, and the targeted native gene is deleted. The exogenous LDH gene is operatively linked to a promoter sequence and a terminator sequence that are each homologous to promoter and terminator sequences, respectively, of the targeted gene.

A gene, promoter or terminator is considered to be "exogenous" for purposes of this invention if it (1) is not found within the genome of the unmodified cell, and (2) is not homologous to genetic material present in the genome of the unmodified cell. As used herein, a gene, terminator or promoter is "native" to the yeast species if it is found (apart from individual-to-individual mutations which do not effect its function) within the genome of the unmodified cells of that species of yeast.

A gene, promoter, terminator or other genomic material is considered to be "homologous" to other genetic material if it is identical, i.e. has at least 80%, 85%, 90%, 91%, 92%, 93%, 94%, 95%, 96%, 97%, 98%, or about 99% identity in nucleotide sequence to the other genetic material, or if not identical, is sufficiently similar to it that it retains its function. Therefore, genetic material is considered to be "homologous" even if contains differences due to, e.g., point mutations, deletions or additions of base pairs, provided that those mutations, deletions or additions that do not affect the function of the genetic material. In the case of flanking sequences, homology is established if the sequence is similar enough to a flanking sequence of the native gene that the flanking sequence can engage in a single crossover event with the flanking sequence of the native gene.

The term "identity," as known in the art, refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is used in the art with regard to a related concept, but in contrast to "identity," "similarity" refers to a measure of relatedness, which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Identity and similarity of related nucleic acids and polypeptides can be readily calculated by known methods. Such methods include, but are not limited to, those described in COMPUTATIONAL MOLECULAR BIOLOGY, (Lesk, A. M., ed.), 1988, Oxford University Press, N.Y; BIOCOMPUTING: INFORMATICS AND GENOME PROJECTS, (Smith, D. W., ed.), 1993, Academic Press, N.Y.; COMPUTER ANALYSIS OF SEQUENCE DATA, Part 1, (Griffin, A. M., and Griffin, H. G., eds.), 1994, Humana Press, N. J.; von Heinje, G., SEQUENCE ANALYSIS IN MOLECULAR BIOLOGY, 1987, Academic Press; SEQUENCE ANALYSIS PRIMER, (Gribskov, M. and Devereux, J., eds.), 1991, M. Stockton Press, N.Y.; Carillo et al., 1988, SIAM *J. Applied Math.*, 48: 1073; and Durbin et al., 1998, BIOLOGICAL SEQUENCE ANALYSIS, Cambridge University Press.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., 1984, *Nucl. Acid. Res.*, 12:387; Genetics Computer Group, University of Wisconsin, Madison, Wis.), BLASTP, BLASTN, and FASTA (Altschul et al., 1990, *J. Mol. Biol.*, 215:403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990, supra). The well-known Smith Waterman algorithm may also be used to determine identity.

Certain alignment schemes for aligning two amino acid or polynucleotide sequences may result in matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide. In some embodiments, the alignment can comprise at least 60, 70, 80, 90, 100, 110, or 120 amino acids of the target polypeptide. If polynucleotides are aligned using GAP, the alignment can span at least about 100, 150, or 200 nucleotides, which can be contiguous.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as three-times the average diagonal; where the "average diagonal" is the average of the diagonal of the comparison matrix being used; the "diagonal" is the score or number assigned to each perfect amino acid match by the particular comparison matrix) and a gap extension penalty (which is usually one-tenth of the gap opening penalty), as well as a comparison matrix such as PAM250 or BLOSUM 62 are used in conjunction with the algorithm. In certain embodiments, a standard comparison matrix (see Dayhoff et al., 1978, *Atlas of Protein Sequence and Structure*, 5:345-352 for the PAM 250 comparison matrix; Henikoff et al., 1992, *Proc. Natl. Acad. Sci USA*, 89:10915-10919 for the BLOSUM 62 comparison matrix) is also used by the algorithm.

In certain embodiments, the parameters for a polypeptide sequence comparison include the following:

Algorithm: Needleman et al., 1970, *J. Mol. Biol.*, 48:443-453;
Comparison matrix: BLOSUM 62 from Henikoff et al., 1992, supra;
Gap Penalty: 12
Gap Length Penalty: 4
Threshold of Similarity: 0

The GAP program may be useful with the above parameters. For nucleotide sequences, parameters can include a gap penalty of 50 and a gap length penalty of 3, which is a penalty of 3 for each symbol in each gap. In certain embodiments, the aforementioned parameters are the default parameters for polypeptide comparisons (along with no penalty for end gaps) using the GAP algorithm.

A "flanking sequence" is a sequence of base pairs upstream (i.e., 5') or downstream (i.e., 3') of a gene. The flanking sequence may be immediately adjacent to the gene, or separated from the gene by an intermediate sequence of base pairs, such as from 1-1000, preferably 1-100 base pairs. The flanking sequences used in the recombinant nucleic acids of this invention are homologous to corresponding flanking sequences of the targeted gene. The length of the flanking sequence is sufficient to permit it to engage in a single crossover event with the corresponding flanking sequence of the native gene. Useful flanking sequences lengths are from about 50 to about 4000 base pairs, preferably about 100 to about 2000 base pairs, especially up to about 1200 base pairs. Upstream flanking sequences preferably contain a promoter, and downstream flanking sequences preferably contain a terminator sequence for the target gene.

In preferred embodiments, the flanking sequences are homologous to and comprise promoter and terminator sequences, respectively, for native yeast Most preferably, integration of the recombinant nucleic acid into the target gene locus in the chromosomal DNA of the yeast genome results in the exogenous LDH gene encoded thereby to fall under the transcription control of the native gene expression regulatory sequences comprising said flanking sequences.

As used herein, the term "promoter" refers to untranscribed sequences located upstream (i.e., 5') to the translation start codon of a structural gene (generally within about 1 to 1000 bp, preferably 1-500 bp, especially 1-100 bp) and which controls the start of transcription of a structural gene or otherwise controls transcription of the gene.

Similarly, the term "terminator" refers to untranscribed sequences located downstream (i.e., 3') to the translation stop codon of a structural gene (generally within about 1 to 1000 bp, more typically 1-500 base pairs and especially 1-100 base pairs) and which controls the end of transcription of the structural gene or otherwise controls transcription of the gene.

A structural gene (such as the LDH gene or selection marker gene, for example) is "operatively linked" to a promoter or terminator, within the context of this invention, if the promoter or terminator, as the case may be, functions after integration in the yeast genome to control the transcription of the structural gene.

The term "transformation" as used herein refers to a change in a cell's genetic characteristics, and a cell has been transformed when it has been modified to contain a new nucleic acid. Thus, a cell is transformed where it is genetically modified from its native state. For example, following transfection, transforming DNA preferably recombines with cellular genomic DNA by physically integrating into a chromosome of the cell. Alternatively, at least transiently (i.e., within 48-96 hrs of cellular transformation), the nucleic acid can be maintained transiently as an episomal element without being replicated, or may replicate independently as a plasmid. A cell is considered to have been stably transformed when the DNA is integrated into the chromosome and is replicated with the division of the cell.

The term "transfection" is used to refer to the uptake of foreign or exogenous DNA by a cell, and a cell has been "transfected" when the exogenous DNA has been introduced inside the cell membrane. A number of transfection techniques are well known in the art. See, e.g., Graham et al., 1973, *Virology* 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, *Gene* 13:197. Such techniques can be used to introduce one or more exogenous DNA species into suitable host cells.

According to the method of the first aspect of the invention, a recombinant nucleic acid is provided comprising an exogenous LDH gene linked to flanking sequences, and at least one selection marker. The term "recombinant nucleic acid" is used herein to refer to any molecule (e.g., nucleic acid fragment, plasmid, or virus) used to transfer protein-coding information to a host cell. Suitable flanking sequences can be obtained by identifying the intended site of integration, such as a target gene in the yeast cell genome, obtaining the sequences that flank that site (using any convenient method, including but not limited to chemical synthesis, recombinant genetic techniques, or in vitro amplification) and incorporating those sequences into the desired position in the recombinant nucleic acid (for example, by covalently linking the flanking sequences 5' and 3', respectively, to the LDH-encoding sequences. The yeast cell is then transformed with the recombinant nucleic acid using any suitable transformation technique. Cells are obtained thereby wherein at least a fragment of the recombinant nucleic acid comprising the LDH gene is integrated into the genome of the yeast cell.

The recombinant nucleic acid includes one or more selection marker genes, which are more preferably under the transcriptional control of their own promoter and terminator sequences. Promoter and terminator sequences for marker genes are preferably not homologous to promoter and terminator sequences of the targeted gene. The selection marker gene(s) and their respective promoters and terminators preferably do not interrupt the sequence of: upstream flanking sequence-LDH gene-downstream flanking sequence. The selection marker gene(s) and respective promoters and terminators are preferentially positioned on the vector upstream (5') to the LDH promoter sequence (and additional flanking sequence, if present).

Preferred yeast species having LDH genes useful for producing the recombinant nucleic acids and cells of the invention and in the practice of the inventive methods include *Lactobacillus helveticus, Pediococcus acidolactici, Lactobacillus casei, Kluyveromyces thermotolerans, Torulaspora delbrueckii, Schizosaccharomyces pombii, Rhizopus oryzae* and *B. megaterium*. In particular, these strains that have suitable L-lactate dehydrogenase genes that can be isolated and used to produce the recombinant nucleic acids of the invention. Two preferred L-lactate dehydrogenase genes are *L. helveticus* and *B. megaterium* L-lactate dehydrogenase.

Typical selection marker genes encode proteins that (a) confer resistance to antibiotics or other toxins, e.g., zeocin (*Streptoalloteichus hindustanus* ble bleomycin resistance gene), G418 (kanamycin-resistance gene of Tn903), hygromycin (aminoglycoside antibiotic resistance gene from *E. coli*), ainpicillin, tetracycline, or kanamycin for host cells; (b) complement auxotrophic deficiencies of the cell, such as amino acid leucine deficiency (Leu2); or (c) supply critical nutrients not available from simple media, e.g., ura3. Preferred selectable markers include the non-limiting examples of zeocin resistance gene, G418 resistance gene, and the hygromycin resistance gene.

Recombinant nucleic acids of the invention may also comprise one or more restriction sites that permit the molecule to be cut to form a linear fragment containing the LDH gene, its promoters and flanking sequences, marker genes and associated promoters and terminators, etc., for insertion into the genome of the yeast cell.

Recombinant nucleic acids of the invention may further contain a backbone portion. Backbone portions advantageously comprise origins or replication (operable in yeast, or bacteria, to permit production of useful amounts of the nucleic acid) and other useful features, and are conveniently obtained from commercially available yeast vectors.

The yeast cell is transformed with the recombinant nucleic acids of the invention. Methods of transforming cells are well known in the art, and can include such non-limiting examples as electroporation, calcium chloride-, or lithium acetate-based methods. Recombinant nucleic acids of the invention used in the transformations can either be digested with particular restriction enzymes prior to use, or undigested. Because the flanking sequences of the LDH gene exhibit a high homology to those flanking the target gene insertion of the upstream flanking sequence/LDH gene/downstream flanking sequence fragment tends to occur at the locus of the target gene.

A target gene is any gene that is,desired to be replaced with the LDH gene. A preferred target gene is a pyruvate decarboxylase gene, as replacing this gene disrupts a competing pathway that produces ethanol. In addition, the pyruvate gene tends to be a active in yeast species, so insertion of the LDH gene into the genome under control of the PDC promoters and terminators tends to produce a mutant that expresses LDH well. Additional preferred target genes are ADH, Leu2 and Ura3.

As a consequence of transforming yeast cells with recombinant nucleic acids of the invention, selecting recombinant cells by growth in media selective for the selection marker, and further growth of the selected transformants under non-selective conditions, recombinant yeast cells are obtained having the exogenous LDH gene comprising the recombinant nucleic acid integrated into the genetic locus of the target gene in the yeast chromosome. As obtained according to the methods of this invention, these cells have deleted the target gene, and the integrated, exogenous LDH gene is inserted into the target gene locus so that it is operably linked and under the transcriptional control of the expression control sequences (such as the promoter and terminator sequences) of the target gene. When the target gene is a PDC gene, cells in which the PDC deletion occurs do not grow well under anaerobic conditions. Thus, colonies of the identified and selected cells can be selected by exposing them to anaerobic conditions. Colonies that do not grow are identified as those in which the PDC deletion has occurred. Similarly, targeted integration into any other target gene can be identified by the phenotype associated with deletion of each of the target genes.

A schematic diagram of the genetic events that may produce this result is shown in FIGS. 17A and 17B. As shown in FIG. 17B, the selection marker gene(s) can be deleted spontaneously together with the deletion of the target gene. Selection of the transformants in which the selection marker genes have been deleted is preferred, since genetically-engineered yeast cells having certain properties, such as increased drug resistance, may create undesirable environmental risks.

The resulting yeast cell is missing the target gene, and contains an exogenous LDH gene integrated into the yeast cell genome at the locus of the target gene. The LDH gene is under the transcriptional control of a promoter sequence and a terminator sequence that is homologous to promoter and terminator sequences of the target gene.

As can be seen from FIG. 17B, the LDH promoter and terminator sequences may be those which were present in flanking sequences contained in the recombinant nucleic acid that was used to transform the cell, or may be those which were originally present in the cell's genome at the site of integration. It is also possible that the target gene terminator is retained with deletion of the terminator sequence that was present in the integration vector.

Yeast cells that are suitable for transformation in the first and second aspects of the invention include those from the genera *Candida, Saccharomyces, Kluyveromyces, Pichia*, and *Hansenula*. Yeast cells that do not accumulate pyruvate, i.e., that naturally metabolize pyruvate to ethanol or other metabolization products, are preferred. Cells from the genera *Candida* and *Kluyveromyces* are particularly preferred. Especially preferred cells are *C. sonorensis* and *K. marxianus*.

Cells of the fifth aspect of the invention are recombinant cells of the species *K. marxianus*. These cells are typically prepared by somewhat different transformation methods, although the methods described above are suitable provided that the target gene is not a PDC gene. In this case, the recombinant nucleic acid is not designed for targeted insertion at the locus of a native PDC gene of the yeast cell. Accordingly, the vector(s) used to transform the cell will not typically contain flanking sequences that are highly homologous to flanking sequences of the native PDC gene of the yeast cell.

The cells of the fifth aspect are typically prepared through two or more transformations, each time introducing a copy of an LDH gene. However, it is possible to construct a recombinant nucleic acid containing multiple LDH genes, thus enabling multiple LDH genes to be inserted in a single step. Thus, the vector(s) used to transform the cell will contain one or more LDH genes, each operatively linked to a promoter and a terminator. As before, the recombinant nucleic acid(s) may also contain various marker genes, each under the control of promoter and terminator sequences that are preferably not PDC promoter and terminator sequences native to the yeast cell.

Suitable LDH genes include those described above with respect to the first three aspects of the invention. *L. helveticus* L-LDH and *B. megaterium* L-LDH genes are preferred. The cells are transformed with multiple LDH genes, i.e., at least two such genes, preferably about 2-10 of such genes, more preferably 2-5 of such genes. The inserted LDH genes may be all the same gene, or may be comprised of two or more different types of LDH gene (i.e., genes obtained from more than one species). Recombinant yeast cells containing two or more copies of *L. helveticus* L-LDH genes, those containing two or more copies of *B. megaterium* L-LDH genes, and those containing at least one copy of each of *L. helveticus* and *B. megaterium* L-LDH genes are preferred.

Suitable promoters for use with the LDH in forming the cells of the fifth aspect include promoters for the yeast genes phosphoglycerate kinase (PGK), glyceraldehyde-3-phosphate dehydrogenase (TDH), pyruvate decarboxylase (PDC) (from species other than *K. marxianus*), triose phosphate isomerase (TP1), transcriptional enhancer factor-1 (TEF), purine-cytosine permease (PCPL3), and alcohol dehydrogenase (ADH). Preferred promoters of the invention include the *S. cerevisiae* PGK promoter and the *S. cerevisae* PDC1 promoter.

Suitable terminators include GAL10 and CYC-1 terminators from *S. cerevisae* or other yeast species.

Suitable selection markers are as described with respect to the first three aspects of the invention.

When transformation is performed in multiple steps, the cells are first transformed with a first vector containing at least one LDH gene. Successfully transformed cells are then selected, generally through the exploitation of properties resulting from the presence of a selection marker. Successful transformants are then transformed one or more additional times, until a final cell having the desired number and type of exogenous LDH genes is obtained.

The transformed yeast cells of the invention are useful for producing lactic acid from carbohydrates in a fermentation process. Fermentation can be conducted using any convenient fermentation process. Typically cells are provided for use with a fermentation medium containing a carbohydrate that the cell is capable of metabolizing to pyruvate, and exposed to conditions under which fermentation occurs. The fermentation medium also contains nutrients (such as sources of nitrogen, phosphorus, sulfur, trace minerals, etc.) that promote the viability of the cells.

The particular carbohydrates that can be used depend on the particular host cell, and whether the host cell has been engineered to metabolize any particular carbohydrate to pyruvate. Hexose sugars such as glucose and fructose, oligomers of glucose such as maltose, isomaltose, maltotriose, starch, and sucrose, maltodextrins and xylose (a pentose sugar) are preferred. Less preferred carbohydrates include galactose, mannose and arabinose.

The temperature during fermentation can be from about room temperature, more preferably from about 30° C., more preferably from about 35° C., to about 55° C., more preferably to about 50° C., even more preferably to about 45° C. The maximum temperature will depend somewhat on the particular host cell. When the host cell is *K. marxianus,* for example, the recombinant cell (of any aspect of the invention) can tolerate relatively high temperatures (such as above 40° C. and up to 50° C., especially up to 45° C.). Another preferred host species, *C. sonorensis,* can tolerate temperatures up to about 40° C. This temperature range provides for the possibility of conducting the fermentation at such higher temperatures (thereby reducing cooling costs) without a significant loss of productivity. Another advantage provided by the good high temperature tolerance is that if the fermentation becomes contaminated with an undesired microorganism, in many cases the undesired microorganism can be selectively killed by heating the fermentation medium to 40° C. or more, especially 45° C. or more, without significantly harming the recombinant cells of the invention.

During fermentation, the concentration of cells in the fermentation medium is typically in the range of about 1-150 g dry cells/liter of fermentation medium, preferably about 3-10 g dry cells/liter of fermentation medium, even more preferably about 3-6 g dry cells/liter of fermentation medium.

During the production phase of the fermentation, in some instances it may be preferred to operate microaerobically rather than strictly anaerobically. Optimum aeration conditions can be established for each microorganism by measuring specific oxygen uptake rates (OUR) and correlating those rates with yield, substrate consumption rates and the rate at which the desired fermentation product is produced. In many cases, yield and rates are optimized within a particular range of OUR. For yeast having a PDC disruption, optimum OUR values tend to be within the range of about 0.8 to about 3.5 mmol $O_2$/dry weight cells/hr. OUR refers to the rate at which oxygen is consumed by the cells during fermentation, and is expressed in units (mmoles or grams) of oxygen per dry weight of cells per unit time, such as mmol $O_2$/dry weight cells/hour. Oxygen consumption is conveniently determined by measuring oxygen introduced into the fermentation and oxygen removed from the fermentation. OUR measurements can be used as a basis to control aeration conditions (notably rate of gas introduction, agitation, proportion of oxygen in the aerating gas, etc.) during the production phase of a fermentation in order to maintain OUR within the range that is optimum for the particular organism. The concentration of dissolved oxygen in the broth is simultaneously maintained at less than 1% of saturation, particularly less than 10 micromol $O_2$/L. In a particularly preferred process, a growth phase of the ferementation is conducted such that the concentration of dissolved oxygen in the broth is reduced to less than 1% of saturation, particularly less than 10 micromol $O_2$/L, for a period of time, such as about 15-90 minutes, prior to the start of the production phase (i.e., switching from aerobic conditions in the growth phase to microaerobic conditions in the production phase.

As lactic acid is produced, the pH of the fermentation medium tends to drop unless a base is added to neutralize all or part of the acid as it forms. In one embodiment of the fermentation process, a neutralizing agent such as calcium carbonate, calcium hydroxide, sodium carbonate, sodium hydroxide, ammonia, ammonium hydroxide, and the like is added to the fermentation broth to maintain the pH within a desired range, typically from about 5.0 to about 8.0, especially from about 5.5 to about 7.5. When such a base is added, the corresponding lactate salt is formed. Recovery of the lactic acid therefore involves regenerating the free lactic acid. This is typically done by removing the cells and acidulating the fermentation broth with a strong acid such as sulfuric acid. A salt by-product is formed (gypsum in the case where a calcium salt is the neutralizing agent and sulfuric acid is the acidulating agent), which is separated from the lactic acid. The lactic acid is then recovered through techniques such as liquid-liquid extraction, distillation, absorption, etc., such as are described in T. B. Vickroy, Vol. 3, Chapter 38 of *Comprehensive Biotechnology*, (ed. M. Moo-Young), Pergamon, Oxford, 1985; R. Datta, et al., *FEMS Microbiol. Rev.,* 1995; 16:221-231; U.S. Pat. Nos. 4,275,234, 4,771,001, 5,132,456, 5,420,304, 5,510,526, 5,641,406, and 5,831,122, and International Patent Application No: WO 93/00440.

Alternatively, the pH of the fermentation may be permitted to drop as lactic acid is produced by the cells. Thus, the pH of the fermentation broth may come within the range of about 1.5 to about 5.0, preferably from about 1.5 to about 4.2, more preferably from about 1.5 to about 3.86 (the pKa of lactic acid), especially from about 2.0 to below 3.86 due to the production of lactic acid. Conducting the fermentation in this manner can provide several benefits, if acceptable productivity and yields are achieved. Costs for neutralizing agents are reduced or eliminated. If the fermentation pH (at the end of the fermentation) is below the pKa of lactic acid, the lactic acid will exist mainly in the acid form. This allows the acidulation step to be eliminated, saving additional process steps, acidulation costs, and disposal costs for salt by-products. Thus, an especially preferred process includes continuing the fermentation until the pH of the fermentation broth falls below 3.86. Lactic acid can be separated from the resulting fermentation broth using methods such as those disclosed in WO 99/19290.

The ability of the cell to withstand a low pH environment provides another mechanism by which contamination from unwanted microorganisms can be eliminated. The culture containing the cell of the invention may be subjected to reduced pH conditions, such as a pH of from about 1.5-4.2, preferably from about 2.0 to 3.86, for a time sufficient to kill any contaminating microorganisms that are not acid-tolerant.

To be commercially useful, the recombinant yeast of the invention should exhibit several characteristics. The yeast should convert a significant proportion of the carbohydrate to lactic acid (i.e., produce a high yield of product). Yeast cells should exhibit a high specific productivity, i.e., product a high amount of lactic acid per weight of cell per unit time. Yeast cells preferably are tolerant to a fermentation pH below about 5.0, preferably from about 1.5 to 4.2, especially from 2.0 to 3.86, while providing good yields and productivities under those conditions. The cells are preferably also tolerant to high concentrations of lactic acid, at pH values of 5.0-8.0 and preferably at pH values from 1.5 to 5.0 or more, preferably from 1.5 to 4.2 and especially from 2.0 to 3.86. This last property allows the fermentation process to use high concentrations of the starting carbohydrate.

In general, it is desirable that the fermentation process employing the recombinant cells of the invention provides some or all of the following features:

A. A yield of at least 30, preferably at least 40, more preferably at least 60, even more preferably at least 75 grams of lactic acid per gram of carbohydrate. The theoretical desired yield is 100%, but practical limits on yields are about 95%.

B. A specific productivity of at least 0.1, preferably at least 0.3, more preferably at least about 0.4, especially at least about 0.5 grams of lactic acid/gram of cells/hour. Specific productivities are desirably as high as possible.

C. A titer (i.e., maximum concentration of lactic acid) of at least 15 grams/liter of fermentation medium, preferably at least 20 g/L, more preferably at least 40 g/L, even more preferably at least 80 g/L, up to 150 g/L, preferably up to about 120 g/L. The temperature of the fermentation medium affects the maximum extent of readily achievable titers somewhat, as highly concentrated lactic acid solutions (i.e., above about 150 g/liter) tend to become very viscous or gel at temperatures below about 35° C. Using a higher fermentation temperature, such as from about 35-50° C., permits higher titers without gelling or undue viscosity build-up.

Cells of the third aspect of the invention have been found to provide yields of 85-95%, specific productivities of 0.5-2g/g/hr and titers of 80-120 g/L when used in a neutral (pH 5.0-8.0) fermentation on glucose. At low pH fermentations, in which the pH is allowed to drop to about 2.8-3.0, cells of the third aspect of the invention have been found to provide yields of 75-81% or more, specific productivities of 0.1-0.4 g/g/hr and titers of 14-40 g/L. In all cases these results have been obtained without optimization of fermentation conditions.

Cells of the fifth aspect of the invention (comprising multiple copies of exogenous LDH genes, and containing an intact native PDC gene) have been found to provide yields of over 40%, specific productivities of 0.4-0.9 g/g/hr, and titers of 40-75 g/L in neutral pH (5.0-8.0) fermentations on glucose. In low pH (final pH of 2.8-3.0) fermentations on glucose, cells of the fifth aspect have provided yields of over 30%, specific productivities of 0.3-0.5 g/g/hr and titers of 20-35 g/L. Thus, cells of the fifth aspect retained their ability to ferment well under low pH conditions. As before, these results have been obtained without optimization of fermentation conditions.

In addition, the fermentation process of the invention preferably achieves a high volume productivity. "Volume productivity" is expressed as amount of product produced per unit volume of fermentation medium per unit time, typically gram of product/liter medium/hr of time. Volume productivities of at least 1.5 g/L/hr, preferably at least 2.0 g/L/hr, more preferably at least 2.5 g/L/hr are desirable. At preferred cell densities of up to 3-6 g cells/liter of fermentation medium, maximum productivities tend to up to about 5.0 g/L/hr, and more typically up to about 4.0 g/L/hr. It is highly preferred to conduct the fermentation so that these volume productivities are achieved when the medium pH, temperature, or both are within the ranges described in the preceding paragraph.

Lactic acid produced according to the invention is useful to produce lactide, a cyclic anhydride of two lactic acid molecules. Depending on the stereoisomer of the lactic acid, the lactide may be D-lactide (made from two D-lactic acid molecules), L-lactide (made from two L-lactic acid molecules) or D-L-lactide (made from one of each L-lactic acid and D-lactic acid molecules). A convenient method of producing lactide from lactic acid is via a polymerization/depolymerization method as described in U.S. Pat. No. 5,142,023 to Gruber et al.

Lactide, in turn, is particularly useful as a monomer for the production of polylactide polymers (PLA) and copolymers. Processes for preparing these polymers are also described in U.S. Pat. No. 5,142,023 to Gruber et al. Preferred PLA products are melt-stable polymers as described in U.S. Pat. No. 5,338,822 to Gruber et al. The PLA may be semi-crystalline or amorphous.

The following examples serve to illustrate certain embodiments of the invention and do not limit it in scope or spirit.

EXAMPLE 1A

Construction of Expression Vectors pNC2, Based on S. cerevisiae ScPGK1 Promoter, and pNC4, Based on S. cerevisiae PDC1 Promoter Expression vector pNC2 (FIG. 1.) was generated by combining the S. cerevisiae ScPGK1 and the S. cerevisiae Gal10 terminator on the pGEM5Z(+) (Promega, Wis.) backbone vector. The S. cerevisiae ScPGK1 and the ScGAL10 terminator was separated by a poly-linker region with the restriction sites Xba1, EcoRI and BamHI for inserting particular genes to be expressed between the yeast promoter and terminator.

The S. cerevisiae ScPGK1 promoter used had the sequence (SEQ ID No. 1):

5'-GCGGCCGCGG ATCGCTCTTC CGCTATCGAT TAATTTTTTT

TTCTTTCCTC TTTTTATTAA CCTTAATTTT TATTTTAGAT

TCCTGACTTC AACTCAAGAC GCACAGATAT TATAACATCT

GCACAATAGG CATTTGCAAG AATTACTCGT GAGTAAGGAA

AGAGTGAGGA ACTATCGCAT ACCTGCATTT AAAGATGCCG

-continued
ATTTGGGCGC GAATCCTTTA TTTTGGCTTC ACCCTCATAC

TATTATCAGG GCCAGAAAAA GGAAGTGTTT CCCTCCTTCT

TGAATTGATG TTACCCTCAT AAAGCACGTG GCCTCTTATC

GAGAAAGAAA TTACCGTCGC TCGTGATTTG TTTGCAAAAA

GAACAAAACT GAAAAAACCC AGACACGCTC GACTPCCTGT

CTTCCTATTG ATTGCAGCTT CCAATTTCGT CACACAACAA

GGTCCTAGCG ACGGCTCACA GGTTTTGTAA CAAGCAATCG

AAGGTPCTGG AATGGCGGGA

AAGGGTTTAG TACCACATGC TATGATGCCC ACTGTGATCT

CCAGAGCAAA GTTCGTTCGA TCGTACTGTT ACTCTCTCTC

TTTCAAACAG AATTGTCCGA ATCGTGTGAC AACAACAGCC

TGTTCTCACA CACTCTTTTC TTCTAACCAA GGGGGTGGTT

TAGTTTAGTA GAACCTCGTG AAACTTACAT TTACATATAT

ATAAACTTGC ATAAATPGGT CAATGCAAGA AATACATATT

TGGTCTTTTC TAATTCGTAG TTTTTCAAGT TCTTAGATGC

TTTCTTTTTC TCTTTTTTAC AGATCATCAA GGAAGTAATT

ATCTACTTTT TACAACAAAT CTAGAATT-3'

This sequence was obtained as a restriction fragment from a proprietary plasmid designated pBFY004. Alternatively, it can be obtained by PCR amplification using S. cerevisiae chromosomal DNA as template and primers designed based on SEQ ID NO: 1.

The S. cerevisiae GAL10 terminator used has the following sequence (SEQ ID NO: 2):

5'-GTAGATACAT TGATGCTATC AATCCAGAGA ACTGGAAAGA

TTGTGTAGCC TTGAAAAACG GTGAAACTTA CGGGTCCAAG

ATTGTCTACA GATTTTCCTG ATTTGCCAGC TTACTATCCT

TCTTGAAAAT ATGCACTCTA TATCTTTTAG TTCTTAATTG

CAACACATAG ATTPGCTGTA TAACGAATTT TATGCTATTT

TTTAAATTTG GAGTTCAGTG ATAAAAGTGT CACAGCGAAT

TTCCTCACAT GTAGGGACCG AATTGTTTAC AAGTTCTCTG

TACCACCATG GAGACATCAA AAATTGAAAA TCTATGGAAA

GATATGGACG GTAGCAACAA GAATATAGCA CGAGCCGCGG

ATTTATTTCG TTACGC-3'

This sequence was obtained as a restriction fragment from a proprietary plasmid designated pBFY004. Alternatively, it can be obtained by PCR amplification using S. cerevisiae chromosomal DNA as template and primers designed based on SEQ ID NO: 2.

The vector pNC4 containing expression cassette based on S. cerevisiae PDC1 promoter and ScGAL10 terminator was constructed and used as a general expression vector. The pNC4 vector is shown in FIG. 2.

The vector backbone of pNC4 is pGEM5Z(+) (Promega Corporation; Madison, Wis.). The S. cerevisiae PDC1 promoter was PCR amplified using the primers PSPDCS1 (5'-

CCA TCG ATA ACA AGC TCA TGC AAA GAG-3'; SEQ ID No: 3) and PSPDCAS2 (5'-GCT CTA GAT TTG ACT GTG TTA TTT TGCG-3'; SEQ ID No: 4) and using chromosomal DNA from *S. cerevisiae* strain GY5098 as the template (ATCC 4005098). Thermocycling was performed by 30 cycles of 1 min. at 94° C., 1 min. at 56° C., 1 min. at 72° C., followed by a final incubation of 7 min. at 72° C. using PfuTurbo DNA polymerase (Stratagene).

The *S. cerevisiae* GAL10 terminator was obtained as described above. FIGS. 2a (SEQ ID No: 37) and 2b (SEQ ID No: 38) depict the fragment comprising of the ScPGK1 promoter and ScGAL10 terminator with multi-cloning sites and the ScPDC1 promoter and ScGAL10 terminator with multi-cloning sites.

EXAMPLE 1B

Construction of the pVR22 Vector Having the G418 Resistance Gene Operably Linked to the *S. cerevisiae* PDC1 Promoter and ScGAL10 Terminator The G418 resistance marker (a bacterial neo$^R$ gene) was cloned and placed under the transcriptional control of a *S. cerevisiae* PDC1 promoter; these constructs were designated as pVR22 (FIG. 3). The G418 resistance gene was amplified by PCR using the Pfu Polymerase (Stratagene, Madison, Wis.) with primers 5'-GCT CTA GAT GAG CCA TAT TCA ACG GGA AAC (5'G fragment; SEQ ID No: 5) and 5'-ATG GAT CCT TAG AAA AAC TCA TCG AGC ATC (3' G fragment; SEQ ID NO: 6), using the plasmid pPIC9K (Invitrogen, Carlsbad, Calif.) as the template. Thermocycling was performed by initially incubating the reaction mixture for 5 min at 95° C., then by 35 cycles of 30 sec at 95° C., 30 sec at 49° C., and 2 min at 72° C., followed by a final incubation for 10 min at 72° C. The PCR product was digested with BamHI and XbaI and an 821 bp fragment was isolated and ligated to the 4303 bp BamHI-XbaI fragment of pNC2. (Example 1A). The resulting plasmid (pVR22; FIG. 3) has the ScPGK1 promoter and ScGAL10 terminator operably linked to the G418 resistance gene.

EXAMPLE 1C

Construction of the pVR29 Plasmid Having the G418 Resistance Gene Functionally Linked to the *S. cerevisiae* ScPGK1 Promoter and ScGAL10 Terminator (pVR29)

The G418 resistance marker (pVR22; Example 1B) was cloned into pNC2 (Example 1A) and the construct was designated pVR29 (FIG. 4). The *S. cerevisiae* ScPGK1 promoter and the *S. cerevisiae* GAL10 terminator were used to express the G418 resistance gene. The G418 resistance gene was amplified by PCR using the Pfu Polymerase (Stratagene, Madison, Wis.) with primers 5'- GCT CTA GAT GAG CCA TAT TCA ACG GGA AAC (5'G fragment; SEQ. ID NO.: 5) and 5'-ATG GAT CCT TAG AAA AAC TCA TCG AGC ATC (3' G fragment; SEQ. ID NO.: 6), using the plasmid pVR22 (Example 1B) as template. Alternately plasmid pPIC9K (Invitrogen, Carlsbad, Calif.) can also be used as template. Thermocycling was performed by initially incubating the reaction mixture for 5 min at 95° C., followed by 35 cycles of 30 sec at 95° C., 30 sec at 49° C., and 2 min at 72° C., followed by a final incubation for 10 min at 72° C. The PCR product was digested with BamHI and XbaI and an 821 bp fragment was isolated and ligated to the 4303 bp BamHI-XbaI fragment of pNC2. The resulting plasmid, pVR29 (FIG. 4) contained the ScPGK1 promoter and ScGAL10 terminator operably linked to the G418 resistance gene.

EXAMPLE 1D

Construction of Plasmids pPS1 (Hygromycin Resistance Cassette), pNC14 (Lh-L-LDH Expression Cassette) and pPS9 (Vector for Lh-L-LDH Integration into Genome for Production of L-Lactic Acid, Using Hygromycin Resistance as Selection Marker)

A recombinant nucleic acid was prepares that conferred hygromycin resistance on transformed yeast cells, and thereby permitted selection of yeast cell transformants comprising a recombinant nucleic acid construct encoding a protein useful for synthesis of lactic acid. The vector, pPS9 (FIG. 5), can be used to integrate the *L. helveticus* L-LDH gene into a yeast genome by selecting hygromycin resistance.

The hygromycin resistance marker (*E. coli* hph) was cloned under the transcriptional control of *S. cerevisiae* PDC1 (pyruvate decarboxylase) promoter. The *E. coli* hph gene that confers resistance to hygromycin B was PCR amplified using the primers 5'HYGXBA1 (5'-AAG CTC TAG ATG AAA AAG CCT GAA CTC AC-3'; SEQ. ID NO. 7) and 3'HYG-BAMH1 (5'-CGC GGA TCC CTA TTC CTT TGC CCT CGG AC-3'; SEQ. ID NO. 8) and using the plasmid pRLMex30 (Mach et al. 1994, *Curr. Genet.* 25, 567-570; Rajgarhia et al. U.S. patent application Ser. No: 10/154.360, filed May 23, 2002, incorporated herein by reference in its entirety) as the template. The hph gene can also be obtained using the same primers with *E. coli* chromosomal DNA serving as the template. Thermocycling was performed at 30 cycles of 1 min at 94° C., 1 min at 56° C., and 3 min at 72° C., followed by a final incubation of 7 min at 72° C. using PfuTurb DNA polymerase (Stratagene, Madison, Wis.). The PCR product was electrophoretically separated on a 0.8% agarose gel and the 1026 bp product isolated. The 1026 bp fragment was then digested with XbaI and BamHI and ligated into the XbaI-BamH1 fragment of pNC4 (Ex. 1A) containing the *S. cerevisiae* ScPDC1 promoter and the ScGAL10 terminators to give the plasmid pPS1 (FIG. 5).

The *L. helveticus* L-LDH gene coding for L-lactate dehydrogenase was cloned under the transcriptional control of a *S. cerevisiae* ScPGK1 promoter. The *L. helveticus* L-LDH gene coding for L-lactate dehydrogenase was PCR amplified using primers PS15S (5'-GCT CTA GAA TTA TGG CAA GAG AGG AAA AAC-3'; SEQ. ID NO. 9) and PS16AS (5'-CGG GAT CCT CAT TGA CGA ACC TTA ACG-3'; SEQ. ID NO. 10), using the plasmid pSO20 (Example 1H; FIG. 10) as template. Alternatively the L-LDH gene can be obtained using the same primers with *L. helveticus* chromosomal DNA as the template. Thermocycling was performed by 30 cycles of 1 min at 94° C., 1 min at 56° C., 3 min at 72° C., followed by a final incubation of 7 min at 72° C. using PfuTurbo DNA polymerase (Stratagene, Madison, Wis.). The 990 bp product was electrophoretically separated on a 0.8% agarose gel and isolated. The PCR product was digested with XbaI and BamHI and ligated into XbaI and BamHI digested vector pNC2 (Ex. 1A) to give the plasmid pNC14 (FIG. 5). pNC14 was digested with SalI and BamHI to give the LhLDH expres-

17 sion cassette. This LhLDH expression cassette was isolated and ligated into the SalI-ClaI fragment of pPS1 resulting in plasmid pPS9 (FIG. 5).

EXAMPLE 1E

Construction of the PVR39 Plasmid Containing the *L. helveticus* LLDH Gene and the G418 Marker pPS9 (EX. 1H; FIG. 5) was digested with SphI and dephosphorylated using shrimp alkaline phosphatase (Roche Diagnostics, Indianapolis, Ind.) per the manufacturer's protocols resulting in a fragment containing the *L. helveticus* LDH expression cassette. pVR29 (Ex. 1C; FIG. 4) was digested with SphI and the 2048 bp fragment containing the G418 resistance gene cassette was separated on a 0.8% agarose gel. These fragments were ligated and the resulting plasmid, pVR39 (FIG. 6) contained the *L. helveticus* L-LDH gene and the G418 resistance gene marker adjacent to each other (FIG. 6).

EXAMPLE 1F

Construction of the pHES and pSEH Plasmids

The pHES and pSEH plasmids were constructed according to PCT application PCT/US/44041 using 0.5 µg of plasmid pGAD424 (as described by Chien et al., 1991, *Proc. Natl Acad. Sci. USA* 88:9578-9582) was digested with the restriction enzyme HindIII. The digested mixture was separated by gel electrophoresis on a 0.8% agarose gel using TBE buffer (Biorad, USA). A 5.9 kbp fragment was then purified from the gel as described in Sambrook et al. (1989, *Molecular Cloning*, second edition, Cold Spring Harbor Laboratory, Plainview, N.Y.). A complementary pair of 92 bp synthetic oligomers with multiple restriction enzyme recognition sites was designed. The first was designated 'fwd HES' oligo and had the following sequence:

5'-CCCAAGCTTG AATTCCCCGG GGGATCCCTG CAGGGTACCA

CGCGTAGATC TACTAGTGCG GCCGCCTCGA GTCTAGAGGG

CCCAAGCTTG GG-3'

(SEQ. ID NO: 11). The second was designated 'comp (SO1) (CMA2)hes' oligo and had the following sequence:

5'-CCAAGCTTGG GCCCTCTAGA CTCGAGGCGG CCGCACTAGT AGATCTACGC GTGGTACCCT GCAGG-GATCC CCCGGGGAA TTCAAGCTTG GG-3' (SEQ. ID NO: 12). 500 nmoles of the two complementary oligomers were annealed to each other by boiling the two oligos together in a water bath for ten minutes (100° C.) and cooled gradually to room temperature. The double stranded 92 bp DNA was digested with HindIII and ligated to a HindIII digested 5.9 kbp fragment of pGAD424 (Clontech, USA). The ligation mixture was used to transform *E. coli* DH10B (electromax cells, Life Technologies, Rockville, Md.) by electroporation as described in Sambrook et al. (Id.). Recombinant *E. coli* was plated on Luria-Bertani broth plates (Difco, USA) and cells containing plasmid were selected using 100 µg/ml of the antibiotic ampicillin (Sigma Chemicals, USA). The plasmid DNA from ampicillin resistant *E. coli* clones were screened to obtain the two plasmids pHES and pSEH. The two plasmids differ in the orientation of the multiple cloning site-synthetic double stranded oligomer with respect to the alcohol dehydrogenase (ADH1) promoter on the vector.

EXAMPLE 1G

Construction of pVR1: Plasmid Containing *L. helveticus* L-LDH for Further Construction of pSO20 and pPS9.

*L. helveticus* L-LDH was isolated as follows. *L. helveticus* cells were obtained from the American Type Culture Collection (ATCC Accession #10797) and grown under standard conditions. Genomic DNA was then purified from the cells using the following protocol.

Two 250 ml sterile flasks containing 50 ml each sterile MRS both (Difco, USA) were inoculated with a single colony (or 5 ml) from a glyercol stock of bacteria. The culture was incubated for 48 hours at 37° C. and agitated throughout at 170 rpm. The culture was transferred to 50 ml sterile blue capped tubes and centrifuged at 3000 rpm for 10 minutes. This pellet was suspended in 50 ml of 12.5% w/v sucrose solution and centrifuged again at 3000 rpm for 10 minutes. The newly formed pellets were resuspended in 5 mls of 12.5% w/v sucrose in a 50 ml sterile blue capped tubes. 5 mls of TES solution was added to the tubes. (For 200 ml TES: 2 ml of 1.0 M Tris (pH 8.0) [10 mM Tris (pH 8.0)] 20 ml of 500 mM EDTA (pH 8.0) [50 mM EDTA (pH 8.0)] 0.584 g NaCl [50 mM NaCl] and filter sterilized before use). 12.5% w/v sucrose solution was added to the tubes and mixed. 300 mg of lysozyme powder (Sigma Chemicals, USA) was added and the mixture was vortexed at 2000_rpm for 1 min. 25 µl mutanolysin solution (Sigma) (conc. 2.2 mgs/ml) was added to the mixture and the mixture was incubated overnight (~10-12 hrs.) at 37° C.

2.5 ml of a 20% SDS solution (Biorad, USA) and 168 µl of a Proteinase K solution (concentration=28 mg/1.4 ml) (Sigma) were added to the mixture, and the resulting mixture was mixed by inversion and incubated at 50° C. for one hour. The cell membrane matter broke up well and solution became translucent. The mixture was diluted with NaCl to obtain a 0.15 M concentration in the tube.

The mixture was transferred to a 50 ml. Oakridge tube and treated with an equal volume of phenol:chloroform:isoamyl alcohol (25:24:1) solution. The resulting mixture was shaken and centrifuged at 10,000 rpm for 10 mins. The aqueous layer was transferred into a clean Oakridge tube and an equal volume of chloroform was added. The mixture was then shaken well and was centrifuged at 5000 rpm for 10 min. The aqueous layer was siphoned into a fresh tube and 25 µl of RNAse (100 mg/ml) was added and mixed by inversion. The resulting mixture was incubated at 37° C. for 15 mins.

2.5 volumes of EtOH was added to the mixture along the sides of the tube, but not mixed. The DNA that formed at the interface was spooled and washed in 70% Ethanol and the mixture was centrifuged at 10000 rpm for 10 minutes. The pellet formed at the bottom was the DNA that was air dried and resuspended in 10 mM Tris-HCl, pH 8.5 in a microfuge tube. The mixture was incubated in the tube at 50° C. until the DNA was in solution (~2-3 hrs).

Primers were designed on the basis of the available sequence in Genbank for the L-LDH from *L. helveticus* (Genbank accession # Z81318). PCR amplifications were performed using Pfu polymerase (Stratagene, Wis., USA). Each reaction contained *L. helveticus* genomic DNA at a concentration of 500 ng, each of 4 dNTPs at a concentration of 0.2 mM, and each of the amplification primers SO22 5'-CCG GGA TCC ATG GCA AGA GAG GAA AAA CCTC (SEQ. ID NO: 13) and SO23 5'-CCA AGA TCT TTA TTG ACG AAC CTT AAC GCC AG (SEQ. ID NO: 14) at 1 uM. Thermocycling was performed by an initial incubation for 10 min at 95° C., followed by 35 cycles consisting of 30 sec at 95° C., 30 sec. at 41° C., and 60 sec at 72° C. A 990 (bp) fragment produced by the reaction was gel purified using conventional procedures and digested with BamHI and BgIII restriction enzymes and then cloned into BamHI and BgIII digested pHES (EX. 1F) to give plasmid pLhLDH-HES. The resulting sequence can be translated into a polypeptide that exhibits excellent homology to known *L. helveticus* L-LDH-encoding gene sequences in Genbank (Accession # Z81318).

Additional primers were designed to introduce NcoI and DraIII restriction sites at the 5' end and 3' end respectively of the *L. helveticus* L-LD gene. PCR amplification reactions were performed using Pfu polymerase (Stratagene, Wis., USA). Each reaction contained pLH-LDH/HES at a concentration of 5 ng, each of 4 dNTPs at a concentration of 0.2 mM, and each of the amplification primers VR1 5'-ATC CAT GGC AAG TAT TAC GGA TAA GGA TCA CCAA (SEQ. ID NO. 15) and VR2 5'-ATC ACG AAG TGT CAC GTA CGG GTT TCG ATG TC (SEQ. ID NO. 16) at 1 µM. Thermocycling was performed by an initial incubation for 10 min at 95° C., followed by 35 cycles consisting of 30 sec at 95° C., 30 sec. at 55° C., and 60 sec at 72° C. A 982 bp fragment produced in the reaction was gel purified using conventional procedures digested with NcoI and DraIII restriction enzymes and cloned into NcoI and DraIII digested pTEF1/Zeo (Invitrogen, Carlsbad, Calif.). The resulting plasmid, pVR1 (FIG. 7), confirmed the *L. helveticus* L-LDH-encoding gene sequence under the control of the *S. cerevisiae* pTEF1 promoter. The *E. coli* EM7 promoter is present, but it is not a necessary component of an integration vector of the invention.

EXAMPLE 1H

Construction of the Plasmid pSO20 for *L. helveticus* L-LDH Plasmid Expression in *K. marxianus*

The plasmid pSO20 was constructed by ligating a BamHI (NEB) digested and shrimp alkaline phosphatase treated (Roche Diagnostics, USA) pUC19 Plasmid (Life Technologies, USA) with a BamHI fragment containing the *L. helveticus* L-LDH gene plus adjacent promoter and terminator sequences obtained by digesting pVR1 (EX. 1F). The resulting plasmid was pSO18 (FIG. 8). pSO18 was then digested with SphI and ligated to the SphI fragment from the pSPHI construct (Chen et al., 1986, "Sequence organization of the circular plasmid pKD1 from the yeast *Kluyveromyces drosophilarum*," Nucleic acids Res. 14: 4471-4481) that contains the pKD1 backbone, resulting in the plasmid pSO19 (FIG. 9). pTEF1/Zeo (Invitrogen, Inc) was digested with XhoI/XbaI to release the *S. cerevisiae* TEF1 promoter, Zeocin resistance gene, and *S. cerevisiae* GAL10 terminator. The ends of this 1195 bp fragment were then filled in with Pfu DNA polymerase (Stratagene, Madison, Wis.). Construct pSO19 was digested with AatII, blunt ends generated with Pfu DNA polymerase, and the resulting fragment treated with shrimp alkaline phosphatase. This 9.3 kbp was then ligated with 1195 bp pTEF/Zeo fragment containing the *S. cerevisiae* TEF1 promoter, Zeocin resistance gene, and *S. cerevisiae* GAL10 terminator. The resulting construct is pSO020. (FIG. 10).

EXAMPLE 1I

Introduction of the *L. helveticus* L-LDH Gene Via Random Integration of the Transformed DNA into the *K. marxianus* Genome A 4.28 kbp fragment containing the *L. helveticus* L-LDH: G418 resistance gene cassette was isolated from pVR39 by digesting the plasmid with SstI and ApaI. The fragment was separated on a 0.8% agarose gel, and used to transform *K. marxianus* (CD21) using an electroporation protocol described below:

A single colony of *K. marxianus* was used to inoculate 50 mL of YPD media (comprising 10 g/L yeast extract, 20 g/L peptone, and 20 g/L glucose in a 250 mL baffled shake flask to an OD600 of 0.1). The culture was incubated for 16 hrs at 30° C. with 250 rpm to a final OD600 of 10. The cells from 10 mL of culture were collected by centrifugation and washed one time with electroporation buffer (10 mM Tris-Cl, 270 mM sucrose, 1 mM MgCl$_2$, pH 7.5). The cells were then resuspended in incubation buffer (YPD+25 mM DTT, 20 mM HEPES, pH 8.0) and incubated at 30° C. with 250 rpm for 30 min. The cells were harvested by centrifugation, washed one time with electroporation buffer, and resuspended in 1 mL electroporation buffer. 400 µL of cells were then transferred to a 0.4 cm electroporation cuvette (BioRad; USA).

pVR39 was digested with SstI and ApaI, and 2 µg of the resulting 4.3 Kbp fragment was added to the cuvette. The cells were then electroporated at 1.8 kV, 1000 Ω, 25 µF. The cells were transferred to 1 mL YPD in a 50 mL screw cap Falcon tube and incubated at 30° C. with 250 rpm for 4 hrs before selective plating on YPD containing 300 µg/mL G418. The transformants were grown at 37° C. for 3 days. The G418 resistant transformants were re-streaked onto fresh selective plates containing 300 µg/mL G418.

Verification of fragment integration into the genome of *K. marxianus* was achieved using PCR primers designed to be homologous to the *L. helveticus* L-LDH gene and a reverse primer homologous to the G418 resistance gene.

(SEQ. ID NO.17)
VR146    5'-GCT GAC TAC CCA GAT TGT AAG GATG-3' and (SEQ. ID NO.18)
VR143    5' CTG CCA GCG CAT CAA CAA TAT TTT CAC-3'

18) were designed to amplify a 2.3 kb product between *L. helveticus* L-LDH and the G418 resistance gene in strains that contain the cassette. The primers do not amplify any fragments in strains that do not contain the cassette.

Thermocycling was performed on transformant colonies using Taq DNA polymerase (Qiagen, USA) by initially incubating the reaction mixture for 2 min. at 94° C., then by 35 cycles of 30 sec at 94° C., 30 sec at 53° C., and 3min at 72° C., followed by a final incubation of 7 min at 72° C. Ten transformants analyzed yielded the expected 2.3 kb PCR product. Two of the ten transformants analyzed showed the proper banding pattern consistent with the integration of one copy of the *L. helveticus* L-LDH gene from pVR39 using Southern blots of the genomic DNA from the ten strains hybridized with a *L. helveticus* L-LDH gene as the probe. One of the two strains was identified as CD484.

EXAMPLE 1J

Introduction of an Additional Copy of the *L. helveticus* L-LDH Gene Via Random Integration of the Transformed DNA into the *K. marxianus* Genome A 4.7 kbp fragment containing the *L. helveticus* L-LDH: HPH resistance gene cassette was isolated from pPS9 by digesting the plasmid with SstI and ApaI. The fragment was separated on a 0.8% agarose gel, and used to transform *K. marxianus* CD484 by electroporation:

A single colony of *K. marxianus* CD484 was used to inoculate 50 mL of YPD media (comprising 10 g/L yeast extract, 20 g/L peptone, 20 g/L glucose and 2% agar in a 250 mL baffled shake flask to an $OD_{600}$ of 0.1). The culture was incubated for 16 hrs at 30° C. with 250 rpm to a final OD600 of 10. The cells from 10 mL of culture were collected by centrifugation and washed once with electroporation buffer (10 mM Tris-Cl, 270 mM sucrose, 1 mM MgCl2, pH 7.5). The cells were then resuspended in incubation buffer (YPD+25 mM DTT, 20 mM HEPES, pH 8.0) and incubated at 30° C. with 250 rpm for 30 min. The cells were harvested by centrifugation, washed once with electroporation buffer, and resuspended in 1 mL electroporation buffer. 400 μL of cells were then transferred to a 0.4 cm electroporation cuvette (BioRad; USA).

pPS9 was digested with SstI and ApaI and 5 μg of the resulting 4.7 Kbp fragment was added to the cuvette. The cells were then electroporated at 1.8 kV, 1000 Ω, 25 μF. The electroporated cells were transferred to 1 mL YPD in a 50 mL screw cap Falcon tube and incubated at 30° C. with 250 rpm for 4 hrs before selective plating on YPD containing 200 μg/mL hygromycin (Invitrogen, Carlsbad, Calif.). The hygromycin resistant transformants were grown at 37° C. for 3 days. The transformants were re-streaked onto fresh selective plates containing 300 μg/mL G418 to ensure that the strain had both resistance genes.

Verification of integration of the new 4.7 kbp fragment of *L. helveticus* L-LDH:G418 cassette was achieved using PCR primers designed to be homologous to the *L. helveticus* L-LDH gene and a reverse primer homologous to the hygromycin resistance gene VR146 (SEQ. ID NO. 17) and VR142 5'-GTG ACA CCC TGT GCA CGG CGG GAG ATG-3' (SEQ. ID NO. 19) were designed to amplify a 2.3 kb product between *L. helveticus* L-LDH and the hygromycin resistance gene in strains that contain the cassette. The primers do not amplify any fragments in strains that do not contain the cassette.

Thermocycling was performed using Taq DNA polymerase (Qiagen, USA) by initially incubating the reaction mixture for 2 min. at 94° C., then by 35 cycles of 30 sec at 94° C., 30 sec at 53° C., and 3 min at 72° C., followed by a final incubation of 7 min at 72° C. Four transformants that were analyzed using PCR described above yielded the expected 1.76 kb PCR product.

The presence of the 4288 bp *L. helveticus* L-LDH:G418 gene from *K. marxianus* CD484 was verified using PCR primers designed to be homologous to the *L. helveticus* L-LDH gene and a reverse primer homologous to the G418 resistance gene VR146 (SEQ. ID NO. 17) and VR143 (SEQ. ID NO. 18) were designed to amplify a 2.3 kb product between *L. helveticus* L-LDH and the G418 resistance gene in strains that contain the cassette. The primers do not amplify any fragments strains that do not contain the cassette.

Thermocycling was performed using Taq DNA polymerase (Qiagen, USA) by initially incubating the reaction mixture for 2 min. at 94° C., then by 35 cycles of 30 sec at 94° C., 30 sec at 53° C., and 3 min at 72° C., followed by a final incubation of 7 min at 72° C. All four of the strains yielded the expected 2.3 kb PCR product.

Southern blots of the genomic DNA of the stains hybridized with a *L. helveticus* L-LDH probe demonstrated that one of the four transformants that gave positive PCR results for G418 and hygromycin cassettes also contained two copies of *L. helveticus* L-LDH gene inserted into the genome. The strain was identified *K. marxianus* CD492 and further analyzed for l-lactic acid production.

EXAMPLE 1 K

Production of L-Lactic Acid in YPD+Glucose Medium in Shake-Flask Cultures

Recombinant strain CD 492 was cultivated in a 250 mL baffled shake flasks containing 50 mL YPD supplemented with 100 g/L glucose. The cells were incubated for 16 hours at 30° C. with 250 rpm to an $OD_{600}$ of 0.1 from YPD agar plates. The flask was then tested for residual glucose using the YSI analysis to ensure that the cells were in exponential growth phase. 4 g/L cell dry weight ("gcdw") equivalents were harvested by centrifugation and resuspended in a 250 mL baffled shake flask containing 50 mL YPD supplemented with approximately 100 g/L glucose and 55 g/L $CaCO_3$. The culture was then incubated at 30° C. with 70 rpm. Samples were withdrawn after time intervals of 0, 12, 24 hours. Cells were removed from the samples by filtration and the supernatant was analyzed for glucose, lactate, pyruvate and ethanol by HPLC. Under these conditions, strain CD 492 produced L-lactic acid that was greater than 99% enantiomerically pure. The final titer was 69 g/L. Volume productivity was 3.6 g/L/hr.

For comparison, strain CD 484 (Example 1I) is cultured under the same conditions. L-lactic acid production was lower and ethanol production was higher than seen with CD 492.

EXAMPLE 1L

Production of L-Lactic Acid in YPD+Glucose Medium in Shake-Flask Cultures

Strain 492 was cultivated in a 250 mL baffled shake flask containing 50 mL YPD supplemented with 100 g/L glucose. The cells were inoculated into shake-flasks to an $OD_{600}$ of 0.1 and the flask was incubated for 16 hours at 30° C. with 250 rpm. The final pH was <3.1. The flask was then tested for residual glucose using YSI analysis to ensure that the cells were in exponential growth phase. 4 g/L cell dry weight equivalent was then harvested by centrifugation and resuspended in a 250 mL baffled shake flask containing 50 mL YPD supplemented with approximately 25 g/L glucose. The culture was then incubated at 30° C. with 70 rpm. Samples were withdrawn at various time intervals and the cells were removed by filtration. Culture supernatant was analyzed for glucose, lactate, pyruvate and ethanol by HPLC.

The L-lactic acid produced was greater than 99+% enatiomerically pure. L-lactic acid titer was 15 g/L and the volumetric productivity was 2 g/L/hr. When strain CD 484 is tested under similar conditions, lactic acid production was lower and ethanol production was higher.

In a separate experiment, a 500 mL baffled shake flask containing 100 mL of YPD+100 g/L glucose was inoculated to an $OD_{600}$ of 0.1 with strain CD492. The shake flask was grown approximately 16 hours at 37° C. with 250 rpm. After ensuring that the cells were in the exponential growth phase, 4.0 g/L cell dry weight equivalent was harvested. The cell pellets were resuspended in 50 mL of YPD+40 g/L glucose and transferred to a 250 mL baffled shake flask. The shake flask was placed at 37° C. with 70 rpm. Samples were withdrawn for HPLC analysis at the end of biomass growth and at 0, 15, 18.5 and 23 hours into the production phase until all glucose was consumed. pH was measured at the beginning and the end of production. Final pH was 3.00+/−0.06.

Strain CD 492 consumed the glucose within 15-23 hours. A sample was taken for free acid analysis at the end of production (when glucose had been completely consumed), and analyzed for total lactic acid, acetate, ethanol and pyruvate. Strain CD 492 produced 32 g/L free lactic acid, 32 g/L ethanol and <1 g/L each of acetate and pyruvate. Free lactic acid was 32 g/L. In all instances, the percentage of acids in their protonated form was at least 97% at the end of fermentation. The yield of lactic acid on glucose was 59%.

Strain CD 484 is evaluated under like conditions. It produced 26-28 g/L free lactic acid, and the yield on glucose was 46-58%.

EXAMPLE 2A

Construction of the pVR24 Plasmid Containing B. megaterium L-LDH for Expression of L-LDH Under the Control of the S. cerevisiae ScPGK1 Promoter B. megaterium DNA encoding the LDH gene was isolated as follows. B. megaterium was obtained from the American Type Culture Collection (ATCC Accession #6458) and grown under standard conditions. Genomic DNA was purified from these cells using an Invitrogen "Easy-DNA" kit according to the manufacturer's protocol. Primers were designed on the basis of the available sequence in Genbank for the L-LDH from B. megaterium (Genbank accession # M22305). PCR amplification reactions were performed using Perkin Elmer buffer II (1.5 mM $MgCl_2$) and AmpliTaq Gold polymerase. Each reaction contained B. megaterium genomic DNA at a concentration of 6 ng/uL, each of 4 dNTPs at a concentration of 0.2 mM, and each of two amplification primers BM1270 and BM179 at a concentration of 1 uM:

(5'-CCT GAG TCC ACG TCA TTA TTC-3'; SEQ. ID NO.20)

(5'-TGA AGC TAT TTA TTC TTG TTAC-3'; SEQ. ID NO.21)

Themocycling was performed by an initial incubation for 10 min at 95° C., followed by 35 cycles consisting of 30 sec at 95° C., 30 sec. at 50° C., 60 sec at 72° C. An 1100 bp fragment produced in the reaction was gel purified using conventional procedures, cloned, and sequenced. The resulting sequence could be translated into a polypeptide that exhibits from homology to known L-LDH-encoding genes, wherein the degree of homology us at least 75%, 80%, 85%, 90%, 91%, 92%, 93%, 94%, 95%, 96%, 97%, 98%, or about 99% sequence identity between the two sequences.

The coding sequence for the B. megaterium LDH was operatively linked to a S. cerevisiae ScPGK1 promoter and a ScGAL10 transcriptional terminator from the plasmid pNC2 (EX. 1A). Two oligonucleotide primers, termed Bmeg5' and Bmeg3', were designed to introduce restriction sites at the ends of the coding sequence of the gene: (5'-GCT CTA GAT GAA AAC (SEQ. ID NO.22)
(5'-GCT CTA GAT GAA AAC ACA ATT TAC ACC-3'; and (SEQ. ID NO.23)
(5'-ATG GAT CCT TAC ACA AAA GCT CTG TCGC-3';.

The amplification reaction was performed using dNTP and primer concentrations described above with Pfu Turbo polymerase (Stratagene, Madison, Wis.) in a buffer supplied by the manufacturer. Thermocycling was performed by initially incubating the reaction mixture for 3 min at 95° C., followed by 20 cycles of 30 sec at 95° C., 30 sec at 50° C., and 60 sec at 72° C., followed by a final incubation for 9 min at 72° C. The product was digested with restriction enzymes XbaI and BamHI and then ligated into the XbaI and BamHI fragment of plasmid pNC2 (Ex. 1A). This ligation resulted in plasmid pVR24, having the ScPGK1 promoter and ScGAL10 terminator operably linked to the B. megaterium LDH coding sequence (FIG. 12).

EXAMPLE 2B

G418 Resistance Marker Plasmids Encoding a B. megaterium L-LDH (pCA3)

The G418 antibiotic selection marker obtained from Invitrogen (Carlsbad, Calif.) was modified and operatively linked to the pyruvate decarboxylase gene promoter and a transcriptional terminator from the yeast S. cerevisiae. In making this construct, the following oligonucleotides were prepared and used to amplify the coding sequence from the plasmid containing the G418 resistance gene insert. Two oligo-nucleotide primers, G5' and G3', were designed based on this sequence to introduce restriction sites at the ends of the coding sequence of the gene:

(SEQ. ID No.24)
5'-AAA TCT AGA TGA GCC ATA TTC AAC GGGA-3'; and (SEQ. ID No.25)
5'-CCG GAT CCT TAG AAA AAC TCA TCG AGC AT'3';.

The G418 resistance gene from the pPIC9K vector (Invitrogen, Carlsbad, Calif.) was amplified by PCR using the G5' and G3' primers of each of 4 dNTPs and Pfu Turbo polymerase. The amplification reaction was performed using dNTP and primer concentrations described above using Pfu Turbo polymerase (Stratagene, Madison, Wis.) in a buffer supplied by the manufacturer. Thermocycling was performed by initially incubating the reaction mixture for 3 min at 95° C., then by 20 cycles of 30 sec at 95° C., 30 sec at 50° C., and 60 sec at 72° C., followed by a final incubation for 9 min at 72° C. The product was digested with restriction enzymes XbaI and BamHI and then ligated into the XbaI and BamHI site of plasmid pNC4 (Ex. 1A).

The B. megaterium LDH gene, operatively linked to the S. cerevisiae ScPGK1 promoter and the ScGAL10 terminator, was introduced into this vector at the SphI site at the 3' end of the ScGAL10 terminator of the G418 gene, resulting in plasmid pCA3 (FIG. 13).

EXAMPLE 2C

Construction of the pVR38 Plasmid Containing the B. megaterium LDH Gene and the Hygromycin Resistance Marker pVR24 (Ex. 2A) was digested with SphI and dephosphorylated using shrimp alkaline phosphatase (Roche Diagnostics, Indianapolis USA) per the manufacturer's protocols, resulting in a fragment containing the B. megaterium LDH expression cassette. pPS1 (Ex. ID) was digested with SphI and the 2259 bp fragment containing the hygromycin resistance gene cassette was separated on a 0.8% agarose gel and ligated to the dephosphorylated pVR24. The resulting plasmid, pVR38 (FIG. 14) contained the *B. megaterium* L-LDH gene and the hygromycin resistance gene marker adjacent to each other.

EXAMPLE 2D

Introduction of the *B. megaterium* LDH Gene Via Random Integration of Transformed DNA into the *K. marxianus* Genome A 4.2 kbp fragment containing the *B. megaterium* L-LDH: G418 resistance gene cassette was isolated from pCA3 by digesting the plasmid with SstI and ApaI. The fragment was separated on a 0.8% agarose gel, and was used to transform *K. marxianus* (CD21) using the electroporation protocol described below.

A single colony of K. marxianus was used to inoculate 50 mL of YPD media (10 g/L yeast extract, 20 g/L peptone, 20 g/L glucose and 2% agar in a 250 mL baffled shake flask to an $OD_{600}$ of 0.1). The culture was incubated for 16 hrs at 30° C. with 250 rpm to a final OD600 of 10. The cells from 10 mL of culture were collected by centrifugation and washed one time with electroporation buffer (10 mM Tris-Cl, 270 mM sucrose, 1 mM $MgCl_2$, pH 7.5). The cells were resuspended in incubation buffer (YPD+25 mM DTT, 20 mM HEPES, pH 8.0) and incubated at 30° C. with 250 rpm for 30 min. The cells were then harvested by centrifugation and washed once with electroporation buffer. The cells were then resuspended in 1 mL electroporation buffer, and 400 µL of cells were transferred to a 0.4 cm electroporation cuvette (BioRad; USA).

2 µg of the 4.2 kbp SstI/ApaI fragment from pCA3 were added to the cuvette and the cells were electroporated at 1.8 kV, 1000 Ω, 25 µF. The cells were then transferred to 1 mL YPD in a 50 mL screw cap Falcon tube and incubated at 30° C. with 250 rpm for 4 hrs before selective plating on YPD containing 300 µg/mL G418. The transformants were grown at 37° C. for 3 days. The G418 resistant transformants were restreaked onto fresh selective plates containing 300 µg/mL G418.

Fragment integration into the *K. marxianus* genome was verified using PCR primers designed to be homologous to the *B. megaterium* L-LDH gene and a reverse primer homologous to the G418 resistance gene. BmLDH3 5'-GTA CGC ATT ACC AAG GCT ATT TTA GAT-3' (SEQ. ID NO. 26) and VR143 (SEQ. ID NO. 18) were designed to amplify a 1.8 kb product between the *B. megaterium* L-LDH and the G418 resistance gene in strains that have the cassette. The primers do not amplify any fragments in strains that do not contain the cassette.

Thermocycling was performed on transformant colonies using Taq DNA polymerase (Qiagen, USA) by initially incubating the reaction mixture for 2 min. at 94° C., then by 35 cycles of 30 sec at 94° C., 30 sec at 53° C., and 3 min at 72° C., followed by a final incubation of 7 min at 72° C. Seven out of ten transformants that were analyzed using PCR yielded the expected 1.8 kb PCR product. Two of the seven PCR positive transformants analyzed showed the proper banding pattern consistent with the integration of one copy of the *B. megaterium* L-LDH gene from pCA3 using Southern blot hybridization of the genomic DNA from the seven strains with the *B. megaterium* L-LDH gene as probe. One of the two strains was identified as CD162.

EXAMPLE 2E

Introduction of an Additional Copy of the *B. megaterium* LDH Gene Via Random Integration of Transformed DNA into the *K. marxianus* Genome A 4.5 kbp fragment containing the *B. megaterium* L-LDH: HPH resistance gene cassette was isolated from pVR38 by digesting the plasmid with SstI and ApaI. The fragment was separated on a 0.8% agarose gel and used to transform *K. marxianus* strain CD 162 using electroporation.

A single colony of *K. marxianus* CD162 was used to inoculate 50 mL of YPD media (comprising 10 g/L yeast extract, 20 g/L peptone, 20 g/L glucose and 2% agar in a 250 mL baffled shake flask to an $OD_{600}$ of 0.1). The culture was incubated for 16 hrs at 30° C. with 250 rpm to a final OD600 of 10. Cells from 10 mL of culture were collected by centrifugation and washed once with electroporation buffer (10 mM Tris-Cl, 270 mM sucrose, 1 mM $MgCl_2$, pH 7.5). The cells were then resuspended in incubation buffer (YPD plus 25 mM DTT, 20 mM HEPES, pH 8.0) and incubated at 30° C. with 250 rpm for 30 min. The cells were harvested by centrifugation, washed once with electroporation buffer, and re-suspended in 1 mL electroporation buffer. An aliquot (400 µL) of the cells was then transferred to a 0.4 cm electroporation cuvette (BioRad; USA).

pVR38 was digested with SstI and ApaI and 5 µg of the resulting 4.5 kbp fragment was added to the electroporation cuvette. The cells were then electroporated at 1.8 kV, 1000 Ω, 25 µF. The electroporated cells were transferred to 1 mL YPD in a 50 mL screw cap Falcon tube and incubated at 30° C. with 250 rpm for 4 hrs before selective plating on YPD containing 200 µg/mL hygromycin (Invitrogen, Carlsbad, Calif.). Transformants were grown at 37° C. for 3 days. The hygromycin resistant transformants were restreaked onto fresh selective plates containing 300 µg/mL G418 to ensure that strain had both the resistance genes.

Integration of the new 4.5 kbp fragment comprising the *B. megaterium* L-LDH:HPH cassette was verified using PCR primers designed to be homologous to the *B. megaterium* L-LDH gene and a reverse primer homologous to the hygromycin resistance gene. BmLDH3 (SEQ. ID NO. 26) and VR142 (SEQ. ID NO. 19) were designed to amplify a 1.76 kb product between *B. megaterium* L-LDH and the hygromycin resistance gene in strains that contain the cassette. The primers do not amplify any fragments in strains that do not contain the cassette.

Thermocycling was performed on transformant colonies using Taq DNA polymerase (Qiagen, USA) by initially incubating the reaction mixture for 2 min. at 94° C., then by 35 cycles of 30 sec at 94° C., 30 sec at 53° C., and 3 min at 72° C., followed by a final incubation of 7 min at 72° C. Nine transformants that were analyzed using PCR methodology described above yielded the expected 1.76 kb PCR product.

Verification of presence of the 4.2 kbp *B. megaterium* 1-LDH :G418 gene that was already present in the strain *K. marxianus* CD162 was achieved using PCR primers designed to be homologous to the *B. megaterium* 1-LDH gene and a reverse primer homologous to the G418 resistance gene BmLDH3 (SEQ. ID NO. 26) and VR143 (SEQ. ID NO. 18) were designed to amplify a 1.8 kb product between *B. megaterium* 1-LDH and the G418 resistance gene in strains that contain the cassette. The primers do not amplify any fragments in strains that do not contain the cassette.

Thermocycling was performed on transformant colonies using Taq DNA polymerase (Qiagen, USA) by initially incubating the reaction mixture for 2 min. at 94° C., then by 35 cycles of 30 sec at 94° C., 30 sec at 53° C., and 3 min at 72° C., followed by a final incubation of 7 min at 72° C. All nine of the strains yielded the expected 1.8 kb PCR product. Southern blots of the genomic DNA from these strains hybridized with the *B. megaterium* LDH as probe indicated that seven of the nine transformants that gave positive PCR results for both the G418 and hygromycin cassettes also contained two copies of *B. megaterium* L-LDH gene inserted into the genome. One of the strains was identified CD355.

EXAMPLE 2F

Production of L-Lactic Acid in YPD+Glucose Medium in Shake-Flask Cultures

Recombinant strain CD 355 was cultivated in the general manner described in Example 1K. Under these conditions, strain CD 355 produced L-lactic acid that was greater than 99% enantiomerically pure. The final titer was 52 g/L. Volume productivity was 1.5 g/L/hr.

For comparison, strain CD 162 was cultured under the same conditions. L-lactic acid production was lower and ethanol production was higher than seen with CD 162.

EXAMPLE 2G

Production of L-Lactic Acid in YPD+Glucose Medium in Shake-Flask Cultures

Strain 355 was cultivated a 250 mL baffled shake flask containing 50 mL YPD media supplemented with 100 g/L glucose. The cells were inoculated into shake-flasks to an $OD_{600}$ of 0.1 and the flask was incubated for 16 hours at 30° C. with 250 rpm. The final pH was <3.1. The flask was then tested for residual glucose using YSI analysis to ensure that the cells were in exponential growth phase. 4 g/L cell dry weight equivalent was then harvested by centrifugation and resuspended in a 250 mL baffled shake flask containing 50 mL YPD supplemented with approximately 25 g/L glucose. The culture was then incubated at 30° C. with 70 rpm. Samples were withdrawn at various times and the cells were removed by filtration. Culture supernatant was analyzed for glucose, lactate, pyruvate and ethanol by HPLC.

The L-lactic acid produced was greater than 99+% enatiomerically pure. L-lactic acid titer was 12 g/L and the volumetric productivity was 1.9 g/L/hr. When strain CD 162 is tested under similar conditions, lactic acid production is lower and ethanol production is higher.

EXAMPLE 3A

Construction of the pBH5a/b Plasmids for the Targeted Integration of DNA into the PDC1 Locus of *K. Marxianus*

The DNA flanking the pyruvate decarboxylase (KmPDC1) gene of *K. marxianus* was cloned into the vector pVR29 (Ex. 1C) to generate a vector for directed DNA integration at the KmPDC1 locus. The final resulting construct was designated pBH5b (FIGS. 15a, b & c). A gene cloned into the SbfI restriction site of pBH5b is operatively linked to the *K marxianus* promoter and terminator.

A 1254 bp fragment of DNA immediately upstream of *K. marxianus* PDC1 was PCR amplified with primers 5'-Flank 5': 5'-CAA GAA GGT ACC CCT CTC TAA ACT TGA ACA-3' (SEQ. ID NO. 27) and 5'-Flank 3': 5'-GTA ATT CCT GCA GGT GCA ATT ATT TGG TTT GG-3' (SEQ. ID NO. 28) using the plasmid pSO21 as the template. Thermocycling was performed by initially incubating the reaction mixture for 2 min. at 94° C., then by 35 cycles of 30 sec at 94° C., 30 sec at 55° C., and 1.5 min at 72° C., followed by a final incubation of 7 min at 72° C. The 1254 bp PCR product was separated on a 0.8% agarose gel and isolated. The PCR product and the pVR29 plasmid (EX. 1C) were both digested with KpnI and SbfI. The digested PCR product was ligated to the 5067 bp pVR29 fragment to give the 6315 bp pBH5a (FIG. 15b). The pBH5a plasmid contains a G418 resistance gene operatively linked to the *S. cerevisiae* ScPDC1 promoter and ScGAL10 terminator and a 1240 bp fragment of DNA homologous to DNA immediately upstream of the *K. marxianus* PDC1 gene.

A 535 bp fragment of DNA immediately downstream of *K. marxianus* PDC1 was PCR amplified with primers 3'-Flank 5': 5'-CCA AGC CCT GCA GGA GAG GGA GAG GAT AAA GA-3' (SEQ. ID NO. 29) and 3'-Flank 3': 5'-CTC GTA ACG CGT GTA CAA GTT GTG GAA CAA-3' (SEQ. ID NO. 30) using the plasmid pSO21 as the template. Thermocycling was performed by initially incubating the reaction mixture for 2 min. at 94° C., then by 35 cycles of 30 sec at 94° C., 30 sec at 55° C., and 45 sec at 72° C., followed by a final incubation of 4 min at 72° C. The PCR product was separated on a 0.8% agarose gel and the 535 bp product isolated. The 529 bp PCR product was digested with SbfI and MluI and the fragment ligated with the SbfI-MluI fragment of pBH5a to give plasmid pBH5b (FIG. 15). The pBH5b plasmid contains 1.2 kb of DNA immediately upstream and 0.5 kb of DNA immediately downstream of *K. marxianus* PDC1 with a unique SbfI site located between the flanking PDC1 sequences, along with a selectable G418 resistance marker operatively linked to the *S. cerevisiae* ScPDC1 promoter and ScGAL10 terminator.

EXAMPLE 3B

Construction of the pBH8 Plasmid for the Targeted Integration of *L. helveticus* 1-LDH gene into the KmPDC1 Locus of *K. marxianus*

The L-lactate dehydrogenase gene from *L. helveticus* was cloned into the SbfI site of pBH5b (Ex. 3A). to create a vector capable of integrating the *L. helveticus* L-LDH into the *K. marxianus* KmPDC1 locus and expressing *L. helveticus* L-LDH using the endogenous *K. marxianus* KmPDC1 promoter and terminator.

The *L. helveticus* L-LDH gene was PCR amplified using the primers L-LDH 5': 5'-ACA AAT CCT GCA GGA TGG CAA GAG AGG AAA AA-3' (SEQ. ID NO. 31) and 1-LDH 3': 5'-TAT CTA CCT GCA GGT CAT TGA CGA ACC TTA AC-3' (SEQ. ID NO. 32) using pPS9 (Ex. 1D) as the template. Thermocycling was performed by 30 cycles of 30 sec at 94° C., 30 sec at 55° C., and 1.5 min at 72° C., followed by a final incubation of 4 min at 72° C. using the Failsafe PCR System (Epicentre, Madison, Wis.). The 971 bp PCR product was separated on a 0.8% agarose gel and isolated. The PCR product was digested with SbfI and ligated to the 6844 bp SbfI-digested pBH5b to give the 7824 bp plasmid pBH8 (FIG. 16). pBH8 contains the *L. helveticus* L-LDH gene operatively linked to the *K. marxianus* KmPDC1 promoter and terminator, along with a G418 resistance marker operatively linked to the *S. cerevisiae* ScPDC1 promoter and ScGAL10 terminator.

EXAMPLE 3C

Construction of *K. marxianus* Strains CD606 by Integration of pBH8 into the KmPDC1 Locus Wild-type *K. marxianus* was transformed with the pBH8 plasmid (EX. 3B). The entire pBH8 plasmid was integrated into the KmPDC1 locus of CD21 between the flanking KmPDC1 DNA immediately upstream of the *L. helveticus* L-LDH gene of pBH8 and the DNA immediately upstream of the KmPDC1 gene on the *K. marxianus* chromosome. The resulting strain, termed CD606, contains the wild-type copy of KmPDC1 as well as a single copy pBH8 integrated at the KmPDC1 locus.

CD21 was used to inoculate 50 mL of YPD media (comprising 10 g/L yeast extract, 20 g/L peptone, 20 g/L glucose and 2% agar) supplemented with 100 g/L glucose in a 250 mL baffled shake flask to an $OD_{600}$ of 0.1. The culture was incubated for 16 hrs at 30° C. and 250 rpm to a final OD600 of 12. Cells from 10 mL of culture were collected by centrifugation and washed once with electroporation buffer (electroporation buffer; 10 mM Tris-Cl, 270 mM sucrose, 1 mM MgCl2, pH 7.5). The cells were then resuspended in incubation buffer (YPD+25 mM DTT, 20 mM HEPES, pH 8.0) and incubated at 30° C. and 250 rpm for 30 min. The cells were harvested by centrifugation, washed once with electroporation buffer, and resuspended in 1 mL electroporation buffer. An aliquot (400 µL) of the cells was then transferred to a 0.4 cm electroporation cuvette. 12 µg of uncut pBH8 in a total volume of 50 µL was added to the cuvette, and the cells were electroporated at 1.8 kV, 1000 Ω, 25 µF. The electroporated cells were transferred to 1 mL YPD in a 50 mL screw cap Falcon tube and incubated at 30° C. and 250 rpm for 4 hrs before selective plating on YPD containing 300 µg/mL G418. Transformants were incubated at 37° C. for 2 days and were restreaked onto fresh selective plates.

Proper integration of pBH8 into the KmPDC1 locus between the flanking KmPDC1 DNA immediately upstream of the *L. helveticus* L-LDH gene of pBH8 and the DNA immediately upstream of the KmPDC1 gene on the *K. marxianus* chromosome was verified using primers PDC1 Chromosome 5': 5'-AAG CAC CAA GGC CTT CAA CAG-3' (SEQ. ID NO. 33) and L-LDH 3': 5'-TCG ATA TCG CTA AGG AAC GCG-3' (SEQ. ID NO. 34). The primers were designed to amplify a 2.7 kb product between chromosomal DNA upstream of the KmPDC1 gene and outside of the homology incorporated in pBH8, and the *L. helveticus* L-LDH gene. Thermocycling was performed by initially incubating the reaction mixture for 2 min. at 94° C., then by 35 cycles of 30 sec at 94° C., 30 sec at 55° C., and 3 min at 72° C., followed by a final incubation of 7 min at 72° C. Four out of ten transformants analyzed by PCR and yielded the expected 2.7 kb PCR product.

PCR using primers designed to amplify the KmPDC1 locus PDC1 5' 5'-CGC AAA GAA AAG CTC CAC ACC-3' (; SEQ. ID NO. 35) and PDC1 3' 5'-CCC ATA CGC TTA TAA TCC CCC-3' (; SEQ. ID NO. 36) gave two products. One product was a 1.7 kb fragment corresponding to *K. marxianus* PDC1, and a second product was a 1.0 kb fragment corresponding to *L. helveticus* L-LDH. Thermocycling was performed by initially incubating the reaction mixture for 2 min. at 94° C., and then by 35 cycles of 30 sec at 94° C., 30 sec at 55° C., 2 min at 72° C., followed by a final incubation of 5 min at 72° C. Further verification of single copy integration was achieved by Southern blot analysis using a G418 resistance gene encoding region as a probe. One of three transformants analyzed had the proper banding pattern consistent with the integration of one copy of pBH8. A strain with one copy of pBH8 located at KmPDC1 locus, as verified by PCR and Southern analysis, was designated CD606.

These results indicated that targeted integration of the transformed pBH8 DNA into the KmPDC1 locus of CD21 had occurred between the KmPDC1 promoter sequences.

EXAMPLE 3D

Construction of *K. marxianus* Strains CD607 and CD 608 from Strain CD606

CD606 was propagated on non-selective media for several rounds of growth to encourage deletion of the target PDC1 gene. A strain was isolated where the KmPDC1 gene has been replaced by the *L. helveticus* L-LDH gene. This strain was also free of the G418 resistance marker gene, and showed a G418 sensitive phenotype, as confirmed by growth inhibition in the presence of G418; loss of the $neo^R$ gene was confirmed by Southern blot analysis. In addition, the strain was also unable to grow anaerobically.

CD606 was plated on YPD agar plates and involved overnight about 16 hrs. at 37° C. A swab of colonies was transferred to fresh YPD agar plates. This procedure was repeated four times. Following the fifth round of non-selective growth on YPD agar plates, six 250 mL baffled shake flasks containing 50 mL YPD supplemented with 100 g/L glucose and 42 g/L CaCO3 were inoculated to an $OD_{600}$ of 0.1 from plates from the fifth round of non-selective growth of CD606. The shake flasks were incubated at 30° C. and 250 rpm for 16 hrs. The cultures were then diluted using serial dilution of a pea-sized swab of colonies into PBS (phosphate buffered saline). Dilutions of this initial suspension of pea-sized colony swab in 1 ml PBS of 10-5, 10-6 and 10-7 were used for on YPD agar plates.

An additional a swab of colonies from the fifth round of non-selective growth on YPD agar plates was suspended in 1 mL PBS (phosphate-buffered saline; 137 mN NaCl, 2.7 mM KCl, 10 mM $Na_2HPO_4$, 2 mM $KH_2PO_4$ pH 7.4), and then subsequently diluted and used to plate for single colonies on YPD agar plates. Single colonies were plated on YPD agar and placed in an anaerobic chamber [Becton Dickinson, "GasPak System" using three gas packs] used according to manufacturers' directions. Following growth for 2 days at 37° C., the anaerobic chamber was opened and colonies that grew anaerobically were marked. The plates were incubated an additional day at 37° C. Colonies that grew aerobically but not anaerobically were transferred to triplicate plates for screening. The screening conditions employed were aerobic YPD plates, anaerobic YPD plates, and YPD plates supplemented with 300 µg/mL G418. Two transformants were identified with the desired phenotype of G418 sensitivity and a lack of ability to grow anaerobically and were designated CD607 and CD608.

Confirmation of replacement of KmPDC1 with *L. helveticus* L-LDH was achieved using primers PDC1 5' (SEQ. ID NO. 35) and PDC1 3' (SEQ. ID NO. 36). The primers designed to amplify the PDC1 locus using chromosomal DNA from CD607 and CD608 as templates. Thermocycling was performed by initially incubating the reaction mixture for 2 min. at 94° C. and, then by 35 cycles of 30 sec at 94° C., 30 sec at 55° C., 2 min at 72° C., followed by a final incubation of 5 min at 72° C. Chromosomal DNA from both strains yielded a single 1.0 kb PCR product corresponding to *L.*

*helveticus*-L-LDH. Southern blot analysis using a probe the entire coding region of the G418 gene designed to hybridize to the G418 gene indicated the absence of the G418 gene is the PCR product. Southern analysis with a KmPDC1 coding probe showed no bands, indicating the absence of the KmPDC1 coding sequence probes designed to hybridize to regions immediately upstream and downstream of KmPDC1. (The probes used were fragments of DNA homologous to regions of the chromosome immediately upstream and downstream of the PDC1 gene. Probes were PCR amplified using oligomers 5' probe=CA110 and CA111; 3' probe=CA112 and CA113.) gave bands with sizes consistent with the replacement of KmPDC1 with *L. helveticus*-L-LDH.

These results indicated that the KmPDC1 gene, along with the pBH8 plasmid backbone containing the G418 resistance marker linked to the *S. cerevisiae* ScPDC1 promoter and ScGAL10 terminator, were lost from the chromosome of CD606, resulting in a strain where the KmPDC1 gene has been exactly replaced by the *L. helveticus* 1-LDH gene flanked by SbfI sites.

EXAMPLE 3E

Production of L-Lactic Acid by CD607 in Complex $CaCO_3$ Buffered Media

The CD607 strain was cultivated in a 250 mL baffled shake flask containing 50 mL YPD media supplemented with 100 g/L glucose and 50 g/L $CaCO_3$, following inoculation to an $OD_{600}$ of 0.1 from YPD agar plates, for 16 hours at 30° C. at 250 rpm. After ensuring that residual glucose remained in the flask and thus that the cells were in exponential growth phase, 4 g/L cell dry weight equivalent were harvested by centrifugation and resuspended in a 250 mL baffled shake flask containing 50 mL YPD supplemented with 100 g/L glucose and 50 g/L $CaCO_3$. The culture was incubated at 30° C. and 70 rpm (48 hours). Samples were withdrawn at various times (0, 8, 24, and 48 hour intervals) and the cells were removed by filtration. Culture supernatant was analyzed for glucose, lactate, pyruvate and ethanol by HPLC.

After 24 hours, strain CD607 had consumed 59-61 g/L of glucose and produced 58-60 g/L of lactate and 0.3 g/L of pyruvate. After 48 hours, strain CD607 had consumed 101-104 g/L glucose and produced 94-99 g/L lactate and 0.4 g/L pyruvate. These lactate titers represent a 90-98% lactate yield on glucose and a volumetric productivity greater then 2.1 g/L hr during the microaerobic production phase. After 48 hours, an insoluble calcium lactate precipitate formed ("caked") due to the high levels of lactate produced in the cultures, preventing further analysis. Enzymatic lactate analysis showed that the lactate was greater than 99% enantiomerically pure L-lactate. No ethanol was detected in cultures of strain CD607, thus indicating the replacement of the only copy of PDC1 by one L-LDH.

By contrast, strain CD 606 (containing the PDC gene and the *L. helveticus* 1-LDH gene, consumed 124 g/L of glucose under the same fermentation conditions and produced 83 g/L of lactate, 20 g/L of ethanol, and 0.2 g/L of pyruvate.

EXAMPLE 3F

Production of Free L-Lactic Acid in Complex Media with No Supplemental Buffering Agents Strain CD607 strain was cultivated in a 250 mL baffled shake flask containing 50 mL YPD media supplemented with 100 g/L glucose, following inoculation to an $OD_{600}$ of 0.1 from YPD agar plates, for 16 hours at 30° C. at 250 rpm. After ensuring that residual glucose remained in the flask and thus that the cells were in exponential growth phase, 2 g/L cell dry weight equivalent were harvested by centrifugation and resuspended in a 250 mL baffled shake flask containing 50 mL YPD supplemented with an additional 40 g/L glucose. The culture was incubated at 30° C. and 70 rpm (72 hours). Samples were withdrawn at various times (0, 24, 47 and 72 hours after the start of production). Culture samples were analyzed for glucose, lactate (total and free acid), pyruvate, glycerol, acetate and ethanol by HPLC. pH was measured at both the start and end of production.

After 72 hours, strain CD607 had consumed 10.8 g/L of glucose and produced 9.1 g/L of lactate, 0.5 g/L acetate and 1.2 g/L of pyruvate. These lactate titers represent a 84% lactate yield on glucose and a volumetric productivity greater then 0.1 g/L hr during the microaerobic production phase. Enzymatic lactate analysis showed that the lactate was greater than 99% enantiomerically pure 1-lactate. No ethanol was detected in cultures of strain CD607. Additionally, no glycerol was detected. The pH of the broth decreased from 6.50 to 3.05 during the production phase due to organic acid production. Measurement of free lactic acid (protonated lactic acid) by HPLC found 9.1 g/L free lactic acid, indicating that essentially all lactic acid produced by CD607 is in its protonated form.

It should be understood that the foregoing disclosure emphasizes certain specific embodiments of the invention and that all modifications or alternatives equivalent thereto are within the spirit and scope of the invention as set forth in the appended claims. All references cited herein are incorporated by reference in their entirety.

We claim:

1. A process for integrating an exogenous lactate dehydrogenase gene into a yeast cell, wherein prior to the integration the cell has a targeted gene at a locus in its genome, comprising the steps of (a) transforming the cell with a recombinant nucleic acid having a lactate dehydrogenase (LDH) gene, flanking sequences upstream and downstream of the LDH gene, and at least one selection marker gene, said flanking sequences being homologous to flanking sequences upstream and downstream of the targeted gene, such that the LDH gene is inserted into the genome of the cell adjacent to the locus of the targeted gene in a single crossover event, (b) selecting for first transformants containing the LDH gene and the selection marker gene, (c) nonselectively growing said first transformants and (d) selecting among such first transformants for second transformants that contain the LDH gene but have deleted the selection marker gene and the targeted gene.

2. The process of claim 1, wherein the flanking sequence upstream of said LDH gene includes a promoter sequence homologous to a promoter sequence of the target gene, and the flanking sequence downstream of said LDH gene includes a terminator sequence of the target gene.

3. The process of claim 2, wherein the target gene is a pyruvate dehydrogenase gene.

4. The process of claim 1, wherein the recombinant nucleic acid further includes a marker gene operatively linked to promoter and terminator sequences.

5. The process of claim 4, wherein the promoter and terminator sequences operatively linked to the marker gene are not native to the yeast cell.

6. A method for producing lactide, comprising culturing a recombinant cell of a yeast species which contains a target gene at a locus in its genome, the cell having an exogenous lactate dehydrogenase (LDH) gene integrated into its genome under the transcriptional control of promoter and terminator sequences functional in the yeast cell, wherein said LDH gene is integrated at the locus of the target gene and the target gene is deleted from the genome of the cell, under fermentation conditions in a medium containing a sugar that is fermentable by the cell, further comprising the step of converting at least a portion of the lactic acid to lactide.

7. The method of claim 6, further comprising the step of polymerizing the lactide to form a polylactide polymer or copolymer.

8. A method for producing lactide, comprising culturing a recombinant cell of the species *K. marxianus* having multiple exogenous lactate dehydrogenase genes integrated into its genome, each under the control of functional promoter and terminator sequences, wherein wherein the genome of the *K. marxianus* cell further contains a functional pyruvate decarboxylase gene, under fermentation conditions in a medium containing a sugar that is fermentable by the cell, further comprising the step of converting at least a portion of the lactic acid to lactide.

9. The method of claim 8, further comprising the step of polymerizing the lactide to form a polylactide polymer or copolymer.

* * * * *